United States Patent [19]

Anderson et al.

[11] Patent Number: 5,186,824
[45] Date of Patent: Feb. 16, 1993

[54] SYSTEM FOR SOLID PHASE REACTIONS

[75] Inventors: Norman G. Anderson, Rockville, Md.; N. Leigh Anderson, Washington, D.C.

[73] Assignee: Large Scale Biology Corporation, Rockville, Md.

[21] Appl. No.: 754,892

[22] Filed: Sep. 4, 1991

[51] Int. Cl.$^5$ ............................................. B01D 15/08
[52] U.S. Cl. ................................. 210/198.2; 210/657; 422/70; 422/135; 422/225
[58] Field of Search ............... 210/635, 657, 658, 656, 210/198.2, 198.3; 422/70, 135, 225

[56] References Cited

U.S. PATENT DOCUMENTS

| | | | |
|---|---|---|---|
| 2,618,471 | 11/1952 | Weigham | 422/225 |
| 3,527,350 | 9/1970 | Tuthill | 210/198.2 |
| 3,701,609 | 10/1972 | Bailey | 210/198.2 |
| 3,944,538 | 3/1976 | Bodansky | 422/135 |
| 4,077,886 | 3/1978 | Fukuda | 210/198.2 |
| 4,116,948 | 9/1978 | Mittenzwei | 210/657 |
| 4,414,108 | 11/1983 | Ito | 210/198.2 |
| 4,422,941 | 12/1983 | Vaughan | 210/198.2 |
| 4,631,211 | 12/1986 | Houghten | 428/35 |
| 4,900,435 | 2/1990 | Anderson | 210/198.2 |
| 4,909,446 | 2/1990 | Anderson | 210/657 |
| 4,969,993 | 11/1990 | Nash | 422/70 |
| 5,039,488 | 8/1991 | Kohr | 210/657 |
| 5,053,454 | 10/1991 | Judd | 422/135 |
| 5,087,369 | 2/1992 | Tanimoto | 210/198.2 |

FOREIGN PATENT DOCUMENTS

| | | | |
|---|---|---|---|
| 0279882 | 8/1988 | European Pat. Off. | 210/198.2 |
| 2017351 | 11/1971 | Fed. Rep. of Germany | 210/198.2 |

OTHER PUBLICATIONS

Abstract for Japan Patent No. 6379895 Apr. 9, 1988.
Anderson, N. G., "An Introduction to Particle Separations in Zonal Centrigues", *National Cancer Institute Monograph No. 21*, pp. 9–39 (1966).
Barringer, H. P. et al., "Zonal Rotors with Removable Seals: Rotors B-X and BX1", *National Cancer Institute Monograph No. 21*, pp. 165–174 (1966).
Goodchild, J., *Bioconjugate Chemistry 2*, (1990), pp. 165–187.
Caruthers, M. H., "Synthesis of Oligonucleotides and Oligonucleotide Analogues", *Oligodeoxynucleotides*, CRD Press, pp. 7–24 (1989).
Gait, M. J. et al., *Nucleic Acids Research 8*, (1980) pp. 1081–1096.
Itakura, K. et al., *Science 198*, (1977) pp. 1056–1063.
Beaucage, S. L. et al., *Tetrahedron Letters 22*, (1981) pp. 1859–1862.
Newton, R., *American Biotechnology Laboratory 7*, (1989) pp. 41–45.
Milton, S. C. F. et al., *International Journal of Peptide Protein Research 36*, (1990) pp. 193–196.
Knorr, R. et al., *Tetrahedron Letters 30*, (1989) pp. 1927–1930.
*Companion to Biochemistry: Selected Topics for Further Study*, pp. 106–107 (1974).
Anderson, N. G. et al., *Analytical Biochemistry 32*, 460, pp. 472–473 (1969).

*Primary Examiner*—Ernest G. Therkorn
*Attorney, Agent, or Firm*—Venable, Baetjer, Howard & Civiletti

[57] ABSTRACT

A rotating processor is disclosed. The apparatus includes a hollow enclosed rotor, a rotor drive, internal space to hold particulate porous reaction or separations media which may be porous, lines connecting the center and periphera of the internal space with the exterior through fluid line seals, valving to control fluid flow, gradient makers, and a microprocessor to control and monitor the entire system. Optionally the rotor may be spun with the axis vertical or horizontal, and may be used as a conventional column at rest. The rotating processor permits any synthetic or separative process utilizing particulate or solid phase supports, or separations involving phases of different density to be accomplished under conditions which facilitate precise control of fluid flow and minimization of both micro- and macro-anomalous flow. A computer-controlled flat multiport valve system is also described to facilitate programmed scheduling of reagents through the rotor.

14 Claims, 21 Drawing Sheets

SYSTEM FOR SOLID PHASE REACTIONS

TECHNICAL FIELD

The present invention relates to a rotating processor system for performing solid phase reactions involving the use of solid phase particulate beds or phase separations to accomplish separations, purification, biopolymer synthesis or enzyme reactions, and in particular, a rotating system for performing reactions on a large scale or preparative level.

BACKGROUND OF THE INVENTION

A variety of separative, synthetic, and enzymatic or otherwise catalytic processes use beds of particulate material with transport of reactants, reagents and products or eluants in solution through the bed. In addition, many reactions are known in which the products are separated by concentration in one of two or more phases. These processes include, among others, ion exchange chromatography, gel filtration, ion exclusion chromatography, affinity chromatography, separations based on hydrophobicity, purification based on hybridization, peptide synthesis, oligonucleotide synthesis, and polysaccharide synthesis including combinations of the last three. These processes may be carried out on a small scale for analytical purposes or process design, and are then often scaled up for preparative work. In nearly all examples the solid phase particulates are packed in a closed column with a porous frit on the lower end, an optional frit at the top, and with fluid-connections at both ends so that liquid can flow in either direction through the bed. To achieve efficiency and high resolution with solid phase supports, all volume elements of all fluids should flow through paths of identical composition and nearly identical length, and all particles in the bed should be exposed to the same succession of liquids under the same conditions.

In all instances involving solid phase systems, some interaction occurs between the solutes run through the bed and the particles composing the bed. This interaction may be based on secondary forces (ionic, hydrophobic, or on immunochemical interactions, or base pairing) or primary valencies as when amino acids or nucleotides are added to a growing chain on the solid phase support, or when immobilized enzymes cleave substrates flowing through the bed, or when enzymes in solution react with substrates attached to the packing. In addition, solvents or reagents of successively differing composition which dissociate adsorbed or otherwise attached bound molecular species, or which cleave off protective groups, or compounds including polymers which have been synthesized on the support may be made to flow through the support. The dissociated or cleaved substances then are free to flow out of the bed in flowing liquid.

It is a common experience that when processes using particulate beds are scaled up for any purpose, resolution and efficiency are lost. At both bench level and preparative level the reactions occurring in and around each particle or element of membrane support should, ideally, be the same. The differences seen during scaling up are primarily in the uniformity of flow through the bed, in the length of the fluid path through the bed, in the length of time a solid phase bead is exposed to a given reagent, and in the volume of spaces above and below the columns where fluid is funnelled into the attached lines, but where, in conventional systems, mixing and loss of resolution may occur. Some of the differences are due to differences in the rate of flow in different small volume elements of the bed termed microanomalous flow, and band tilting and mixing in end spaces, termed macroanomalous flow.

In addition to microanomalous flow, which is largely due to differences in the size and shape of individual bed, particles and in local packing density and geometry, density differences and density inversions between sequentially employed solutions may also prevent ideal flow since ordinarily no attention is paid to liquid density differences. As previously demonstrated in the centrifugal fast chromatograph (U.S. Pat. No. 4,900,435 and U.S. Pat. No. 4,900,446), careful and rational control of density and use of density gradients will control both macro- and micro-anomalous flow if separations are carried out in a centrifugal field. The basic principles of centrifugal stabilization of density gradients, and of reversal of flow to regenerate columns, also in a centrifugal field, have therefore been previously described. The centrifugal fast chromatograph is an analytical device in which a number of columns are run in parallel using very small samples.

In chromatographic separations, more capacity is needed at the end of the column where the sample is applied, and the thickness of the initial sample zone is partially dependent on column capacity. As successive peaks are eluted, and as they move down the column, less column capacity per unit length is required. Thus, for chromatography, advantages accrue if the column is in the form of a sector, with the sample applied to the large end, and the effluent withdrawn at the narrow end. In a zonal centrifuge (National Cancer Inst. Monograph No. 21, 1966) flow is arranged to be radial, and may be from the edge of a sector-shaped compartment toward the center. The desired flow configuration can be achieved by the present invention.

The requirements for peptide or oligonucleotide syntheses are quite stringent. Antisense oligonucleotides, which are complimentary to RNA or DNA strands of cells, hold the promise of controlling specifically the expression of individual genes, and therefore are of interest as anti-viral agents against HIV and other pathogens, for controlling and even reversing genetic diseases, and for treating cancer—all by translational or hybridization arrest; and by serving as carriers for active groups. To achieve specificity in intracellular hybridization, oligonucleotides approximately 15-18 or more nucleotides long are required. Since native or natural oligonucleotides are rapidly degraded in a biological environment, a variety of modified oligonucleotides have been proposed (*Bioconjugate Chemistry* 2:165 (1990)). Kilogram quantities of highly purified and sequence-specific oligonucleotides (so-called oligos) will be required for large scale animal and clinical trials, and ultimately for clinical use. Oligos are now synthesized in milligram to gram scales with existing bench top equipment. At present, approximately 10 grams of solid support such as controlled pore glass is required for the synthesis of 1 gram of crude material. To synthesize 1 kilo in a single operation would, therefore, require 10 kilos of support, at a cost estimated variously at between $300,000 and $1,000,000 dollars. Clearly, methods for reducing cost and increasing yields are of interest for the synthesis of not only oligonucleotides but also peptides and polysaccharides. Cost reductions and yield enhancements are also desired for other preparative and separative processes.

The most important consideration in oligonucleotide synthesis is yield of pure product, which is dependent on the efficiency of the coupling reaction, the absence of failure sequences, and on minimizing side and degradative reactions. Hence great effort has been expended on the development of efficient chemical procedures and reagents, and on optimizing the time required for each step in the synthesis cycle. The effect of overall efficiency is illustrated by calculating the overall yields for different effective coupling cycle efficiencies. If the average cycle efficiency is 99%, the yield after 20 cycles (which would yield an oligo 21 nucleotides long, since the first or "seed" nucleotide is already attached to the solid support at the outset) would be 83% of the theoretical maximum one. For cycle efficiencies of 98%, and 95%, the yields would fall to 67%, and 36%. Clearly every factor affecting yield is important.

Oligonucleotide synthesis typically involves a series of eleven steps (including washes), the first of which is deprotection of the seed nucleotide (generally removal of a dimethoxytrityl group which protects a terminal reactive group on the deoxysugar of a nucleotide). This is done in acid, and the acid and cleaved trityl group are removed by three washes which also involve a change of solvent from dichloromethane to dry acetonitrile. Nucleotide addition is then done using an activated nucleotide such as a phosphite triester, for example, a deoxynucleoside 3'-phosphoramidite in the presence of an activator such as tetrazole. The addition reaction is very rapid and essentially complete in five minutes (*Oligonucleotides*. J. Cohen, ed., CRC Press, 1989, pp 7-24). After a further wash, those reactive nucleotides remaining (i.e., those to which no nucleotide was added in the previous coupling step) are capped with acetic anhydride. Following an additional wash, an aqueous oxidizing solution is added to oxidize the phosphorous of the added nucleotide, and the support is again washed with a change of solvent from acetonitrile to dichloromethane. This cycle of solutions is repeated for each addition. For the synthesis of an oligo 21 nucleotides long (a so-called 21 mer), 221 or more discrete solutions flow through the solid phase reaction bed.

Several of these solutions are incompatible. Thus, exclusion of water is essential in the coupling step, but the oxidation solution is 20% water by volume. The deprotection solution removes trityl groups, but deprotection must be prevented during the coupling step when the presence of a trityl group on the added nucleotide is essential. The iodine from the oxidizing step must also not be present during coupling, and the capping reagents must be absent between deprotection and coupling. Hence there is extensive washing between the reactive reagents. All of the reagents are expensive, and those remaining after synthesis must be suitably disposed of, also at considerable expense. Any advance which will reduce the volume of reagents required without decreasing yield is therefore very desirable. Recently (Japanese Patent No. 6,379,895) the efficient synthesis of a 90 nucleotide long oligomer (a 90 mer) has been demonstrated without washing between steps. This appears to be due to efficient exchange of one solution with another with minimum reagent trailing, and suggests that if the flow of solutions through a solid support bed could be very precisely controlled and trailing of one solution into the next minimized, that wash volumes could be either diminished or eliminated.

The reaction times involved in specific synthetic steps also create problems during scale up of oligonucleotide synthesis. Deprotection is usually done in 3 minutes, coupling (nucleotide addition) in 5, capping in 2, and oxidation in 1, with washes lasting either 0.5 or 1 minute. If a bed volume is scaled up to 1 liter, for example, it will be difficult to achieve flow rates which will allow such rapid solution changes. Further, reagents diffuse into and out of the pores and interstices of solid phase particles at rates which depend on both the particle and pore sizes, the temperature, the molecular weights of the solutes, and the viscosity of the solvent and are never instantaneous. When one solvent succeeds another in a porous or adsorbent bed, there will therefore be some trailing of adsorbed or included solutes from the previous solution. Hence means for controlling flow, for preventing non-ideal flow, and for keeping interfaces between succeeding fluids as sharp as possible are essential. If the very same schedules used on a bench scale are to be applied to a very large system, then very fast flow rates and large volumes of solution would be required.

The reason for the time limitations on some of the steps is either that side reactions accompany excess dwell time, or activated ingredients become exhausted. An objective in scale up, therefore is to provide sufficient reaction time to carry a reaction essentially to completion, but insufficient time for deleterious reactions to occur.

Similar requirements and limitations occur in the solid phase synthesis of peptides. With other uses of packed beds, scale up involves loss of resolution for reasons mentioned, and usually some dilution of the product.

Some stages of a sequential series of steps in a separation or synthesis are more time dependent than others. Chromatographic separations are generally dependent on the rate of diffusion of the sample components into and out of the chromatographic beads, affinity separations on the rate of diffusion of the substance being purified and the binding energy between the ligands in solution and the adsorbing surfaces, while synthetic procedures depend on the rate of synthetic reactions. However the efficiency of each of these processes are improved if both microanomalous and macroanomalous flow are prevented. Other steps, such as pH changes during regeneration, temperature change, or solvent changes between steps can also be accomplished much more rapidly and efficiently if flow is optimized. Further, it is advantageous to be able to change the flow rates markedly during a procedure without producing disturbances in flow. In addition, excess reagent is required in many systems where many and long fluid lines are required to connect and interconnect complex valve systems.

In conventional procedures using particulate beds, careful attention must also be given to removing gas bubbles which may already exist in the packing, and in preventing their formation from dissolved gasses. In some instances, degassing of solutions is required.

Scale up of biosynthetic and bioseparative processes therefore involves problems of scale which reduce yields, and degrade separations. These and other problems are addressed by the centrifugal processor of the present invention.

SUMMARY OF THE INVENTION

These problems are addressed by the present invention of a system for solid phase reactions comprising a hollow-bowl rotor enclosing a solid support matrix, means for introducing and removing fluids from outside the rotor to the rotor center and to the rotor edge, and means for generating and introducing fluids of differing densities such that fluid phases or layers of differing densities are introduced into the rotor during rotation. During operation of the system, the fluid phases moving toward the center of the rotor or the edge of the rotor are kept separate, depending on the density of each fluid phase relative to the other fluid phases in the rotor. Furthermore, the operation of the system may be under the control of a microprocessor to monitor and adjust such parameters as rotor speed, direction of flow, densities of liquids, and the entry of fluids into and out of the rotor.

The apparatus includes a hollow enclosed rotor, a rotor drive, internal space to hold particulate porous reaction or separations media which may be porous, lines connecting the center and periphera of the internal space with the exterior through fluid line seals, valving to control fluid flow, gradient makers, and a microprocessor to control and monitor the entire system. Optionally, the rotor may be spun with the axis vertical or horizontal, and may be used as a conventional column at rest. The rotating processor permits any synthetic or separative process utilizing particulate or solid phase supports, or separations involving phases of different density, to be accomplished under conditions which facilitate precise control of fluid flow and minimization of both micro- and macro-anomalous flow. A computer-controlled flat multiport valve system is also described to facilitate programmed scheduling of reagents through the rotor.

DETAILED DESCRIPTION OF THE PREFERRED EMBODIMENTS

Figure 1:
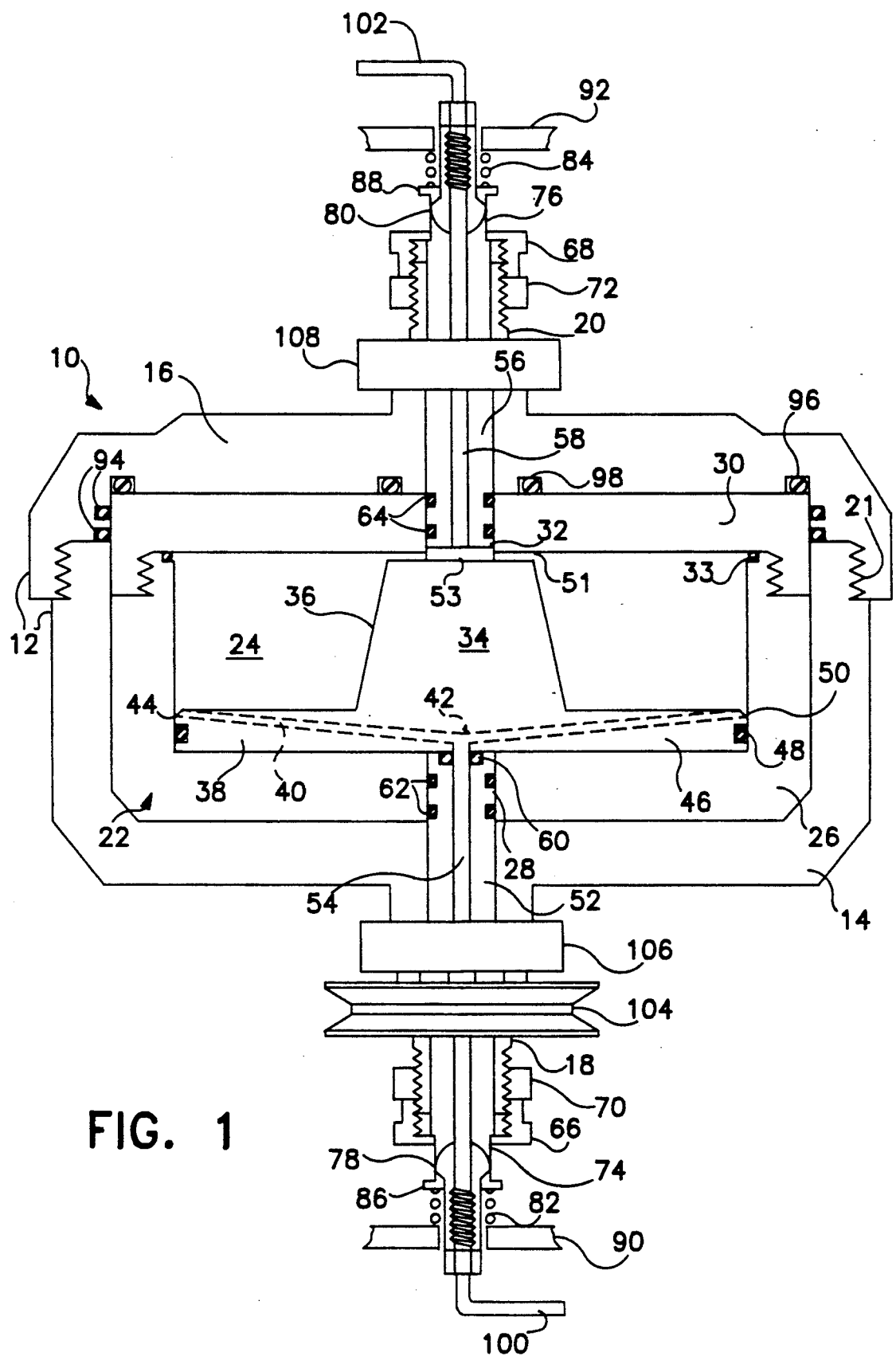
FIG. 1 illustrates a sectional view of a centrifugal processor according to the present invention.

The system of the present invention provides a means for performing reactions or separations involving a solid phase. Thus, the present invention provides a means for performing all ion exchange, gel filtration, chromatographic separations, polymer syntheses of any sort, hybridization or enzyme-based reactions using solid phase supports, and similar reactions in which the separations involve phase separations, in a centrifugal system on a preparative scale, with resolution and efficiency comparable to that obtained on an analytical scale. Such solid phase reactions or separations are generically referred to herein as solid phase reactions.

These reactions are achieved in the centrifugal processor according to the present invention (described in greater detail below) using a hollow-bowl centrifuge rotor to contain a solid phase support (also referred to herein as solid phase material, solid phase matrix or particulate bed), and with the combination of centrifugal force and liquid density differences used to control and stabilize liquid flow through the particulate bed. The internal volume may be optionally divided into sector-shaped compartments, and the rotor may be optionally operated with the axis vertical or horizontal, or the axis may be changed during use.

Separate fluid lines connect the center of the rotor and the edge of the rotor to the exterior. Liquids may therefore be caused to flow through the rotor in either a centrifugal or a centripetal direction. The seal may be coaxial, with both combined in one seal at one end, or two separate fluid lines and fluid line seals may be used, with one at each end of a hollow rotor axis shaft.

The rotors may include sintered filters in the edge and center flow lines so that particulate solid phase material is retained in the rotor regardless of the rate of liquid flow, or the direction of liquid flow through the rotor.

The solid phase support may be in the form of particles of homogeneous or heterogeneous size, in the form of filaments, membranes arranged as flat discs or as circumferential layers or in any other arrangement, membranes incorporating interactive particles, heteropolymeric plastics with reactive groups, hollow filaments of any arrangement, or any combination of these.

Thus, samples and reagents may be pumped either to the rotor center, or the edge, and flow may be reversed at any time. Stability of reagent bands is maintained by flowing into the spinning rotor liquids of increasing density when flow is centripetal (i.e., in through the edge line), and by flowing in liquids of decreasing density when flow is centrifugal (i.e., through the center line). Thus, in a synthetic process for example, a series of reagents of successively increasing density may be introduced through the edge line, and, when an upper density limit of the series has been reached, the direction of flow may be reversed and the entire rotor contents may be displaced outwardly by pumping one light fluid in through the center line, or, after the flow reversal, a series of solutions of decreasing density may be introduced through the center line, displacing denser fluid out the edge line.

Thus, for a procedure involving a large number of separate steps, each involving the introduction of a separate solution, the entire set may be one long series of either increasing density or decreasing density, or may be divided into two series, one increasing sequentially in density, the other sequentially decreasing in density, with flow direction reversals between the two groups. For oligonucleotide or peptide synthesis the latter approach is useful, and flow reversal occurs after the rotor is full of either the most dense or the least dense solutions. This is done partly because these solutions must be run through in excess to insure complete washing, are usually solvent wash solutions, and are cheaper than solutions containing active reagents.

For other procedures, including chromatography, flow reversal may be more advantageously done before and after one solution, usually one used for bed regeneration, such as in ion exchange separations. A sample may be introduced to the rotor edge in a solution slightly denser than that already in the rotor, and be followed by still denser solutions which elute the separated solutes. At the end of the separation an even denser regenerating solution may be introduced from the rotor edge and washed completely through the rotor chamber and packed bed. At this point flow is reversed, and light solvent run in to complete conditioning and washing of the bed. This light solvent is then followed, after a second flow reversal, by a slightly denser sample solution or band, which is in turn followed by the eluting continuous- or step-gradient.

When the separation requires the use of solutions or gradients which decrease in density, the flow direction is from the rotor center to the rotor edge, with the densest solution in the rotor initially. The sample is then introduced to the rotor center in a solution slightly lighter than that already in the rotor, and is then followed by an eluting continuous- or step-gradient of decreasing liquid density.

When a liquid which is denser than that in the rotor is introduced to the edge of the rotor chamber, it flows rapidly and evenly over the entire circumferential inner edge surface, and is held there by centrifugal force, thus eliminating most of the head space volume of a conventional large column. Circumferential flow may be through the bed itself, or may be through a porous material lining the inner wall of the rotor chamber. This flow may also be facilitated by tapering the rotor walls to give a larger diameter at the end of the rotor to which the edge line is attached. The core may also be tapered or angled to facilitate rapid concentration of outflowing iso-dense zones through the center line, as is done in the zonal ultracentrifuge. Centrifugal force and control of liquid density insure that fluids move rapidly to their expected radii in the rotor during rotation. Thus, succeedingly denser fluids will displace each other toward the rotor center. For example, if a density difference of 0.1 gm/mL exists between two liquids, and if the centrifugal field is 1,000×g, the liquids in the rotor will behave as if their density differences were equal to the product of density difference and centrifugal force, i.e. 100 g/mL, which is more than the difference between the densities of uranium metal and water. This force is continuously applied to liquids of relatively low viscosity, providing a continuing driving force to achieve uniform density at any given radius and height in the rotor.

At the rotor core, iso-dense zones tend to flow upward and are funnelled into the core exit line. The core may include surfaces to facilitate this concentration and exit flow similar to those previously developed for zonal centrifuges, i.e., surfaces which, in polar coordinates have the properties of a funnel. (*Natl. Cancer Inst. Monograph* 21, pp 241–244, 1966). The rotor wall may also be tapered to facilitate zone concentration during flow through the rotor in a centrifugal direction, especially when the rotor is operated with the axis horizontally disposed.

When a hollow-bowl rotor filled with liquid is rotated, and when liquid is caused to flow through it either centrifugally or centripetally, part of the liquid will acquire a radial velocity different from that of the rotor at a corresponding radius due to the well-known Coriolis forces. Thus, if at constant rotor speed, liquid is caused to flow from the rotor internal wall edge to the rotor center, and if it has been accelerated to the inner edge tangential velocity during introduction, it will accelerate relative to the rotor as it flows toward the center. The reverse will occur during centrifugal flow. Thus, tangential velocity differences introduced by Coriolis forces can cause anomalous flow in a fluid bed. This source of anomalous flow is minimized either by the presence of a particulate bed as employed in the present invention, or by attaching radially arranged vanes to the rotor core as is done in the zonal ultracentrifuge.

If two fluids of different density are introduced into a spinning hollow bowl rotor without mixing, the interface between them will be described by a parabola of rotation according to the following equation:

$$L = r^2 w^2 / 2g$$

where L is the distance in a vertical direction from the apex of the parabola in centimeters, r is the radius in centimeters, and w is the rotor speed in radians per second.

This means that in a vertical axis rotor a denser liquid flowing in the lower edge line will form a zone of rotation which is thicker at the bottom periphera than at the top, and that the reverse will be true when the same zone approaches the core. The net effect is to assist in funnelling liquid both into and out of the rotor efficiently. As rotor speed is increased, interfaces between zones of different density will approach vertical.

Instances occur when the same solid phase support material is advantageously suspended to form a fluidized bed to promote one reaction of a series, and is then allowed to sediment and is treated as a column and a succession of reagents passed through it. This is the case with some procedures for oligonucleotide and peptide synthesis where the solid phase is suspended in a excess of synthon (e.g., activated amino acid or nucleotide) to promote coupling; but is then treated as a packed bed during other steps. The centrifugal system of the present invention can be adapted to fill both of these functions. In this case the rotor is not completely filled with solid phase support initially. The rotor is operated with the axis horizontal, and by slow rotation, the solid support is completely and evenly suspended. The speed of rotation is then increased and the particulate support is centrifuged to the wall to form an even annulus of packed material. As rotation is continued, solutions may be passed in the edge line and out the center (or vice versa) in density order sequence as described above. The core may include short vanes to aid in subsequent particle resuspension and to prevent mixing due to Coriolis forces, or the core may absent, and outflow through the center line driven purely by density differences, even in the presence of Coriolis force driven tangential flow.

When, in the synthesis sequence, the time comes again for resuspension, the rotor is first filled during rotation with the solution to be used (usually a coupling solution containing a synthon), and then decelerated to the slow speed at which resuspension occurs. Resuspension may be assisted by changing the direction of slow rotation at intervals. Resuspension is then maintained by agitation for the period required, after which the particles are again centrifuged to the wall, and the subsequent solutions changes made. The resuspension interval would thus occur once each synthesis cycle. Note that the rotor may be arranged to operate horizontally during parts of a cycle, and vertically during others. The rotor may also be designed to operate as a column in a vertical configuration without rotation should that be advantageous.

With a horizontal axis rotor, the rotor wall and the core edge may be tapered to facilitate zone concentration during flow at a speed such that centrifugal force at the core edge is greater than 1 xg.

In either oligonucleotide or peptide synthesis, the synthons are mixed with activating agents immediately before use because the mixture has only a relatively short half life. In practice, short bursts of the synthon and activator solution are introduced into the reactor flow line, and mixed immediately before or during flow through the solid support. In a large solid phase bed, it is difficult to be sure that all levels of the bed have been exposed to equal concentrations of activated synthon. In the system of the present invention, a gradient may be formed of narrow zones of successively denser liquids which contain alternate zones of activator and synthon. These may be arranged so that mixing occurs by diffusion during flow through the bed, resulting in the formation of activated synthon continuously at all levels or at all radii.

An alternative method for insuring more uniform activation is to mix chilled synthon and activator immediately before entry into the rotor, running the mixture very rapidly into the rotor, and allowing it to warm up in place. Warming will occur chiefly at the edge, decreasing the density of the solution in this area resulting in its flow toward the center due to the effect of centrifugal force on liquids of slightly different density. This will result in convection in the rotor volume, and gradual even warming of the entire volume.

Furthermore, temperature alone may be used to stabilize a liquid zone in a rotor, and the temperature of inflowing lines may be easily controlled. Thus, if fluid of continually decreasing temperature flows in through the edge line, each element of the inflowing fluid will be very slightly denser than that already in the rotor, producing a temporarily stabilized gradient. The reverse procedure—a gradient of increasing temperature—may be used to stabilize liquid flowing in through the center line.

Valving systems, fluid reservoirs, and gradient producing systems are included to control the composition and density of fluid flowing into the rotor, while monitors for liquid density (g/ml), optical absorbance, pH and other factors may be included in the exit line. Valves are also included to reverse flow through the rotor, and the system may be configured so that any and all reagents may be caused to flow into either end. In addition, rotor speed controls and indicators may be provided, and all steps in a process monitored and controlled automatically by a microprocessor.

Oligonucleotide and peptide synthesizers typically include large numbers of valves, and many flow lines of various lengths, all of which can produce mixing and cross contamination between suceeding fluids. One object of the present invention is to provide zero hold up multiport valves which may be positioned immediately above and immediately below the rotating processor with short fluid lines between. The lower valve is connected to the rotor edge line, and the upper valve is connected to the upper center line. Fluids flowing downward will always be in descending density order and will be stable within the lines, while fluids flowing upward will be in ascending density order and will also be stable to gravity. Thus, in both cases density differences and ordinary gravity are used to minimize mixing.

Centrifugal processors may also be used in series to achieve different functions depending on the particulate beds employed, and the conditions used. For example an oligonucleotide may be synthesized in one centrifugal processor, the product cleaved and passed through a desalting rotor to change the solvent, into a third centrifugal processor where the product may be adsorbed preferentially, contaminants selectively eluted, and the purified product then desorbed and recovered in a small volume. Optionally, the product may be further passed into a hollow-bowl rotor attached to a vacuum pump for concentration by flash evaporation or lyophilization.

A wide variety of reagents are used for separations and syntheses involving solid phases. The interior surfaces of the rotor, and all surfaces in contact with reagents must be resistant to them. For many chromatographic separations done at essentially neutral pH anodized aluminum, titanium, carbon fiber or glass fiber rotors may be used. For relatively low speed systems glass filled fluorocarbon plastics, or homogeneous plastics including polycarbonate, or PEEK, may be used. Hybrid rotors may also be made with plastic liners of resistant materials surrounded by load-bearing materials of metal or strong composite materials. However, for oligonucleotide synthesis and for peptide synthesis a very unusual and corrosive set of reagents is involved. For peptides these include among others dichloromethane, dimethylformamide, acetic anhydride, pyridine, piperidine, methanol, 2-propanol, ethyl ether, 95% trifluoroacetic acid, and for some procedures anhydrous HF. For oligonucleotide synthesis the reagents include among others dichloromethane, dichloroacetic acid, acetonitrile, acetic anhydride, dimethylaminopyridine, tetrahydrofuran, lutidine, water, dissolved iodine, and concentrated ammonia. The choice of materials for rotor, seal, and valve construction and O rings for sealing all components are therefore very limited, and includes polypropylene (for limited use), fluorocarbon plastics, a new class of fluoroelastomers (Kalrez), and glass. Some parts of the system may be composed of stainless steel or titanium. The most direct solution to the problem of materials is to construct rotors of metal, encasing an inner sealed fluorocarbon liner which extends to include the fluid-line seals. All fluid contacts are then limited to fluorocarbon plastics, fluorocarbon elastomers, and glass. The inner liner is removable and may be prepacked with solid support particles and furnished and removed as a sealed package.

In a centrifugal field of sufficient force, gas bubbles are rapidly moved to the axis of rotation and may then flow out of the rotor. The hydrostatic pressure also generally increases the solubility of gases in liquids, providing a further means for minimizing bubble formation.

The axial ratio of rotors of the present invention may vary from so-called pancake rotors which have a large diameter relative to length, to long tubular rotors whose diameter is only a fraction of their length. Rotors tend to be unstable when the axial ratio approaches 1, hence this ratio is avoided.

For any of the applications listed, the entire centrifugal system may be enclosed in a suitable shield to contain rotor fragments in case of rotor explosion or leakage.

The Rotating Processor System

FIG. 1 illustrates a preferred embodiment of a centrifugal processor 10 in which selected solid phase reactions may be performed. The centrifugal processor 10 includes a rotor body 12 formed from a lower cylindrical member 14 and end cap 16, each having an integral axial tubular extension 18 and 20, respectively. The lower cylindrical member 14 and end cap 16 have corresponding threads 21 so that the end cap 16 may be easily removed to provide access to the interior of the rotor body 12. Disposed within the rotor body 12 in close-fitting relation to the interior walls of the rotor body 12 is a removable chemically-resistant liner 22 that defines a chamber 24. The resistant liner 22 has a cylindrical lower member 26 with a lower axial opening 28 and an upper liner liner end cap 30 which has an upper axial opening 32 axially aligned with lower opening 28. The two components 26 and 30 of the liner 22 are sealed by an O-ring 33.

Disposed within the liner 22 is a central core member 34 which includes a core post 36 and lower core disc 38. The lower core disc 38 has a plurality of radial fluid lines 40 which extend through the core disc 38 preferably at an incline as shown. The lines 40 connect a lower axial fluid port 42 to an upper outer edge 44 of the core disc 38, that is spaced away from the inner wall of the liner 22, thereby forming an opening adjacent the inner wall. The lower portion 46 of core disc 38 is sealed against the liner 22 with O-ring 48. Porous, removable frit material 50 disposed in the radial fluid lines 40 at the edge 44 allows fluid to flow from the chamber 24 through the lines 40 but retains particulate material held in the rotor chamber 24. Core post 36 has upper radial connecting fluid lines 51 which converge out an axial center and which have removable frit material 53. Removable frit material 53 is added after the rotor body has been packed with support particles during rotation.

A lower post 52 of chemically-resistant material having an inner fluid line 54 is fitted in the lower tubular extension 18 and the lower axial opening 28 of the liner 22. Likewise, a similar upper post 56 having an inner fluid line 58 is fitted in the upper tubular extension 20 and the upper axial opening 32 of the liner 22. The fluid lines 54 and 58 of the posts 52 and 56 are aligned, respectively, with the lower fluid port 42 of the core disc and the axial center of the converging radial lines 51. Lower post 52 is sealed against the port 42 by O-ring 60. Lower post 52 is also sealed against lower liner member 26 by O-rings 62. Upper post 56 is sealed inst upper liner end cap 30 by O-rings 64.

The lower post 52 and upper post 56 are pressed against the core member 34 by respective knurled nuts 66 and 68 which are threaded to the tubular extensions 18 and 20 and which, when tightened, press against end recesses in the posts 52 and 56. The pressurizing nuts 66 and 68 are locked in place by backup nuts 70 and 72, respectively. Lower and upper rotating seal surfaces 74 and 76 are integral with the lower and upper posts 52 and 56 and rotate with the rotor body. Lower and upper hemispherical static seals 78 and 80 are pressed against the rotating surfaces 74 and 76 by lower and upper springs 82 and 84, with force transmitted between collars 86 and 88 and static members 90 and 92. Additional sealing O-rings 94, 96 and 98 are provided to prevent leakage of fluid from the rotor.

External lower and upper fluid ,lines 100 and 102 may be coupled to the fluid lines 54 and 58 to allow fluid to enter and exit the rotor body 12. The lower tubular extension 18 is coupled to a drive pulley 104 that may be drivingly connected to a motor in order to rotate the rotor body 12. Lower and upper thrust bearings 106 and 108 are coupled to the lower and upper tubular extensions.

Figure 2A:
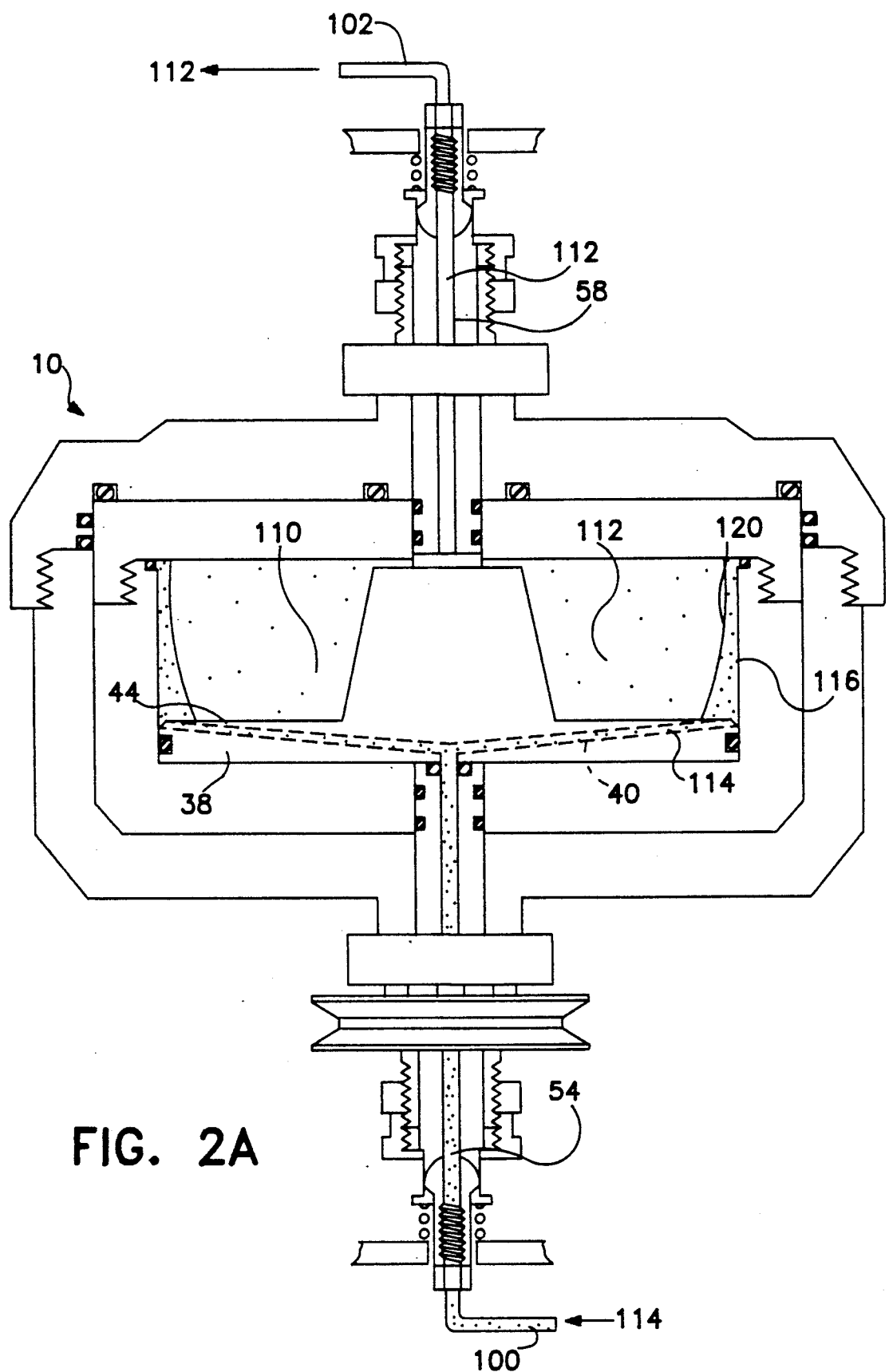
FIGS. 2A-2D illustrate sequential steps of an example of the use of the centrifugal processor of FIG. 1 when completely packed with a solid support material.

FIGS. 2A–2D illustrate the behavior of liquids that are introduced sequentially in increasing density to the core edge 44 of the rotor body during rotation. In FIG. 2A, the rotor body chamber is entirely filled with solid phase particulates 110. A light fluid 112 (not indicated by shading) is initially present in interstices between the particulates and in the upper fluid line 58. A denser fluid 114 is introduced into the rotor body chamber through the lower fluid line 54, core member radial fluid lines 40, and past the edge 44 of the core disc 38. Once in the rotor body, the denser fluid 114 assumes a circumferential position 116, displacing light fluid 112 out through upper fluid line 58 and upper external line 102. The interface 120 between the light solution 112 and the denser solution 114 assumes the configuration of a parabola of rotation.

Figure 2B:
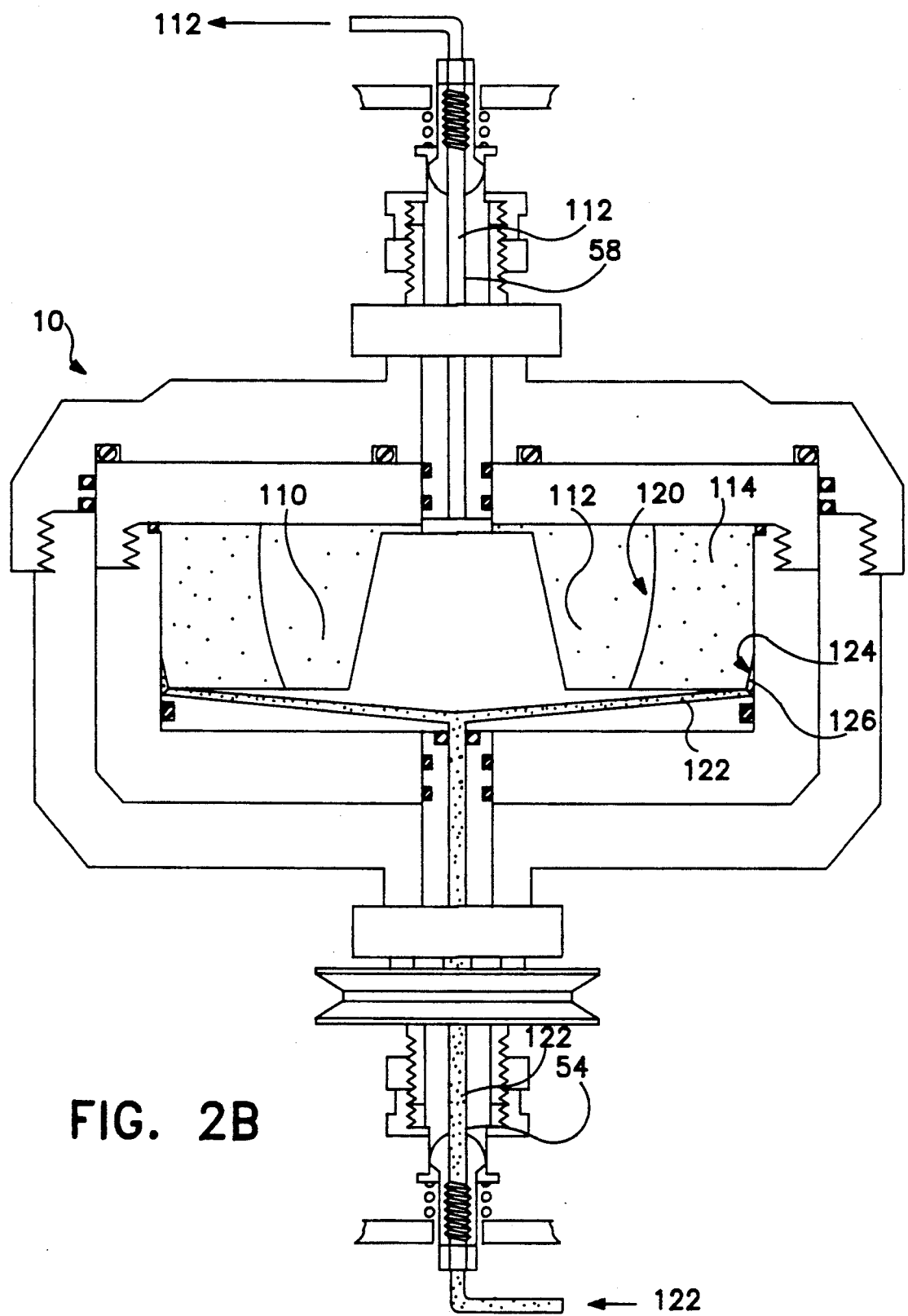

In FIG. 2B, a still denser solution 122 is introduced to the rotor body chamber through the lower fluid line 54, centripetally displacing the solutions 112 and 114, with a portion of the light solution 112 passing out of external line 102. The interface 124 between the denser solution 122 and solution 114 also assumes the configuration of a parabola of rotation 126 at the lower edge of the interior rotor chamber.

Figure 2C:
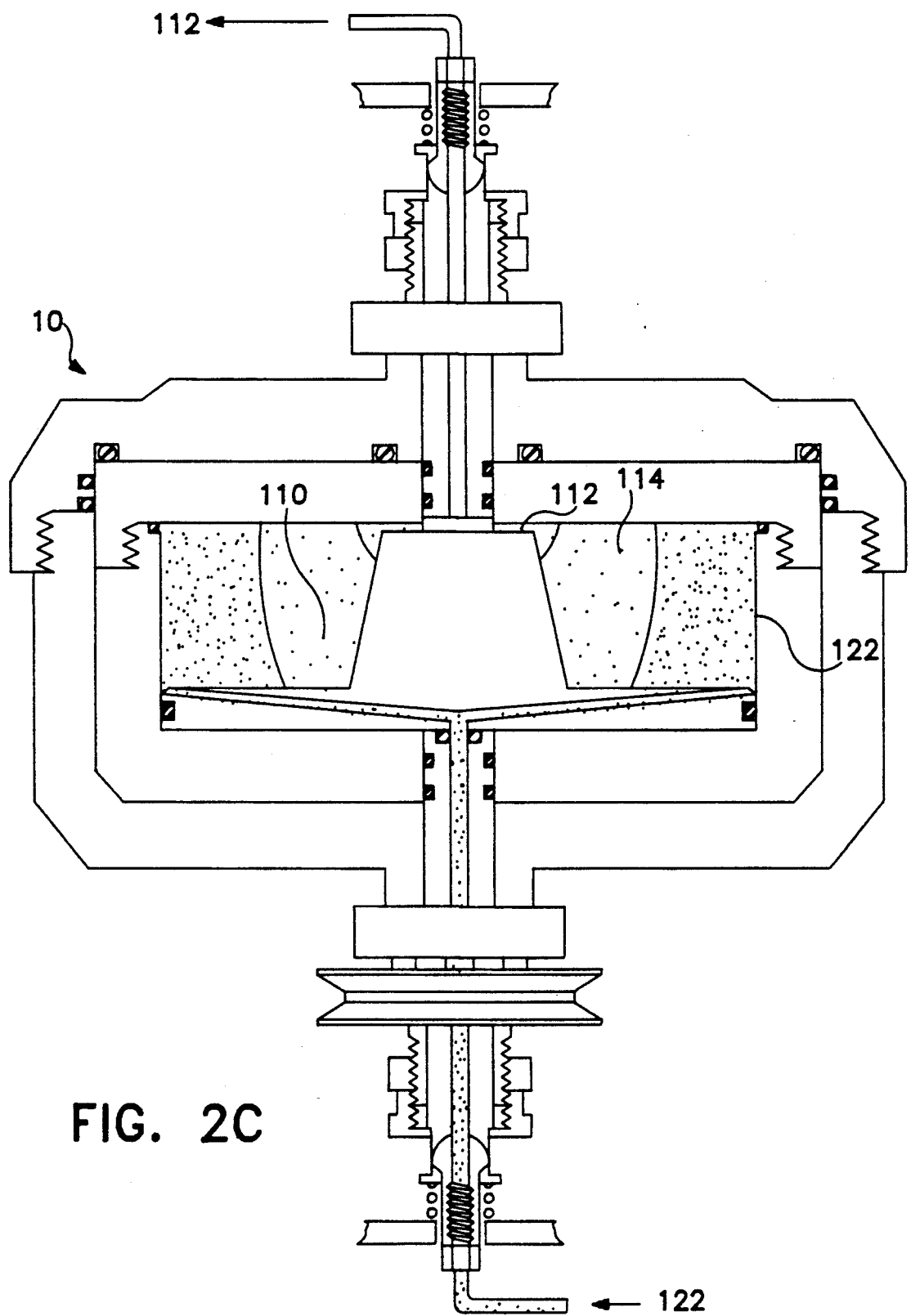

In FIG. 2C, dense solution 122 is continually pumped into the rotor body chamber so that it occupies a larger fraction of the rotor chamber volume, the intermediate density solution 114 occupies a position closer to the rotor body axis, and nearly all of the light solution 112 has passed out of the rotor body chamber through the upper lines and seal.

Figure 2D:
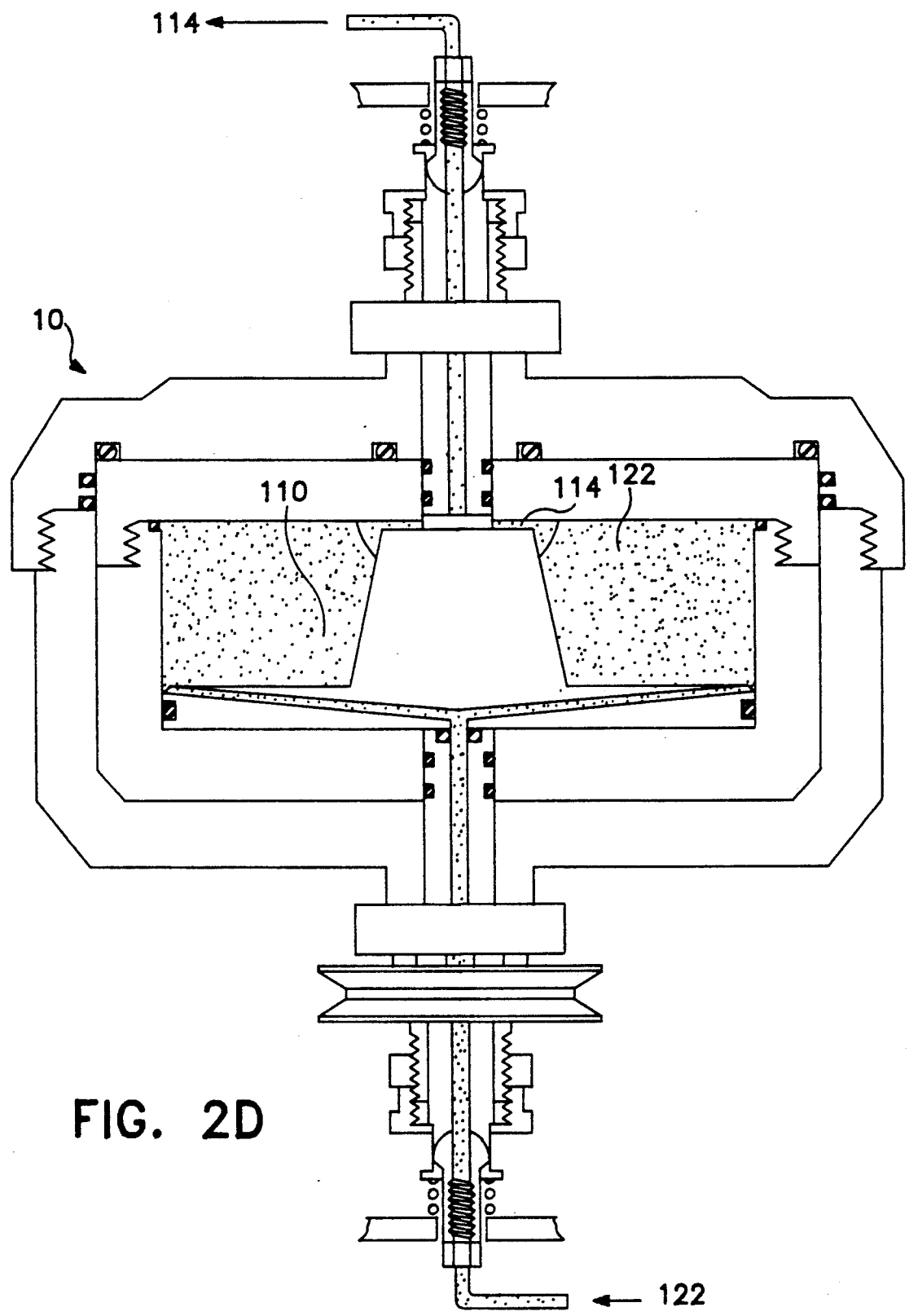

In FIG. 2D, the rotor is almost entirely filled with inflowing dense solution 122, and nearly all of intermediate solution 114 has passed out of the rotor body chamber through the upper fluid lines. Succeedingly still denser solutions may be introduced to displace, in order, all preceding solutions, none of which need occupy an entire rotor chamber volume. The reverse process can be achieved by reversing the order of solutions added so that less-dense solutions are added sequentially, and by adding them through the upper line, provided that the rotor is initially filled with dense solution 122.

Figure 3A:
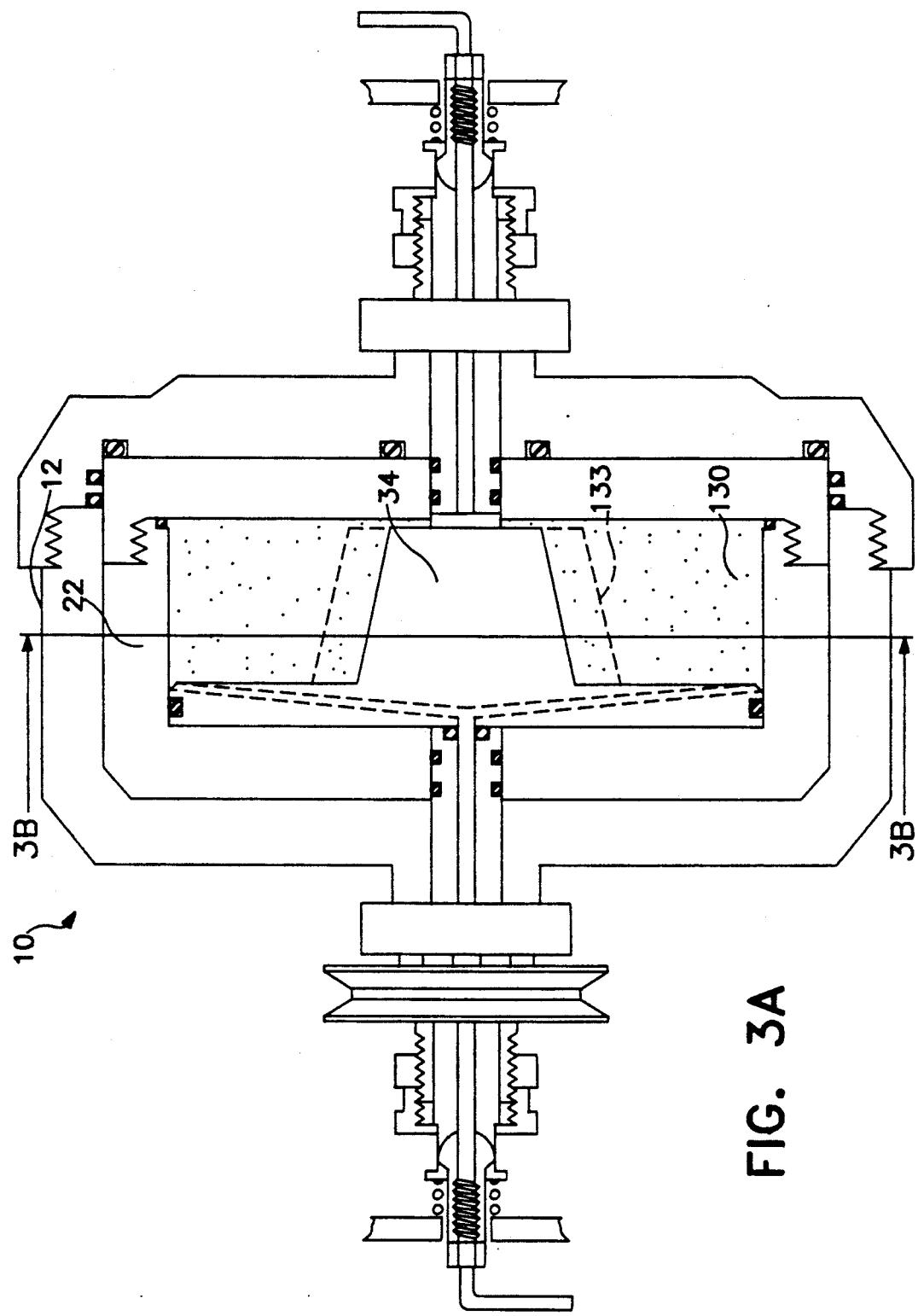
FIGS. 3A-3E illustrate sequential steps of an example of the use of the centrifugal processor of FIG. 2 when operable to rotate about a relative horizontal axis.
Figure 3B:
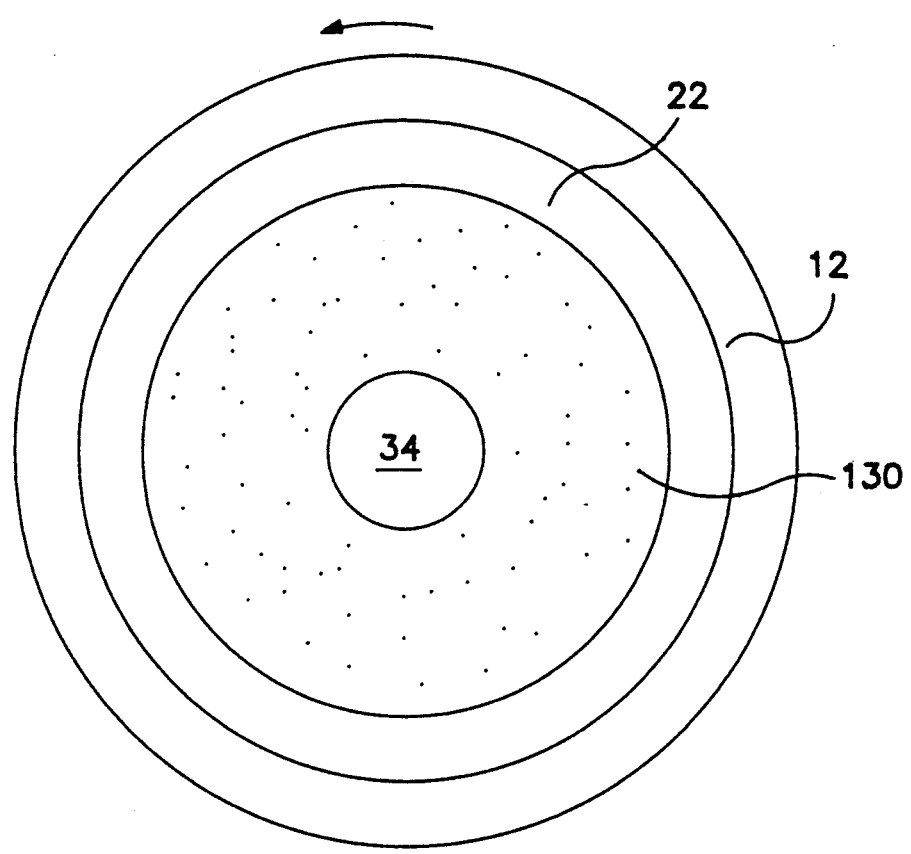
Figure 3C:
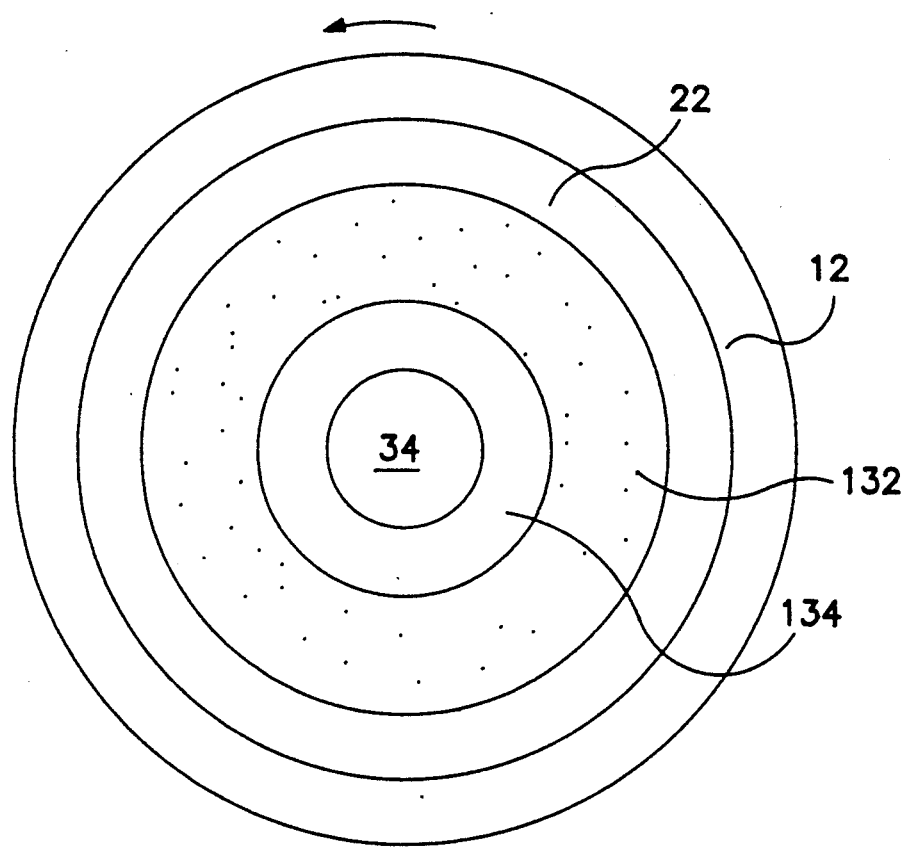

FIGS. 3A-3E illustrate the use of the rotating processor 10 operated with the axis of rotation in a horizontal position. The rotor body chamber is filled with a suspension 130 of solid phase support medium under conditions such that if the support were sedimented it would not completely fill the rotor chamber (as shown in FIG. 3C). Suspension of the solid phase support is achieved by slowly rotating the rotor about its axis, and may be assisted by short vanes 133 (shown in phantom) attached to the core member 34. During a coupling reaction step in, for example, the synthesis of DNA, the solution would contain a synthon, and suspension achieved by slow rotation would contribute to the efficiency of coupling.

Figure 3D:
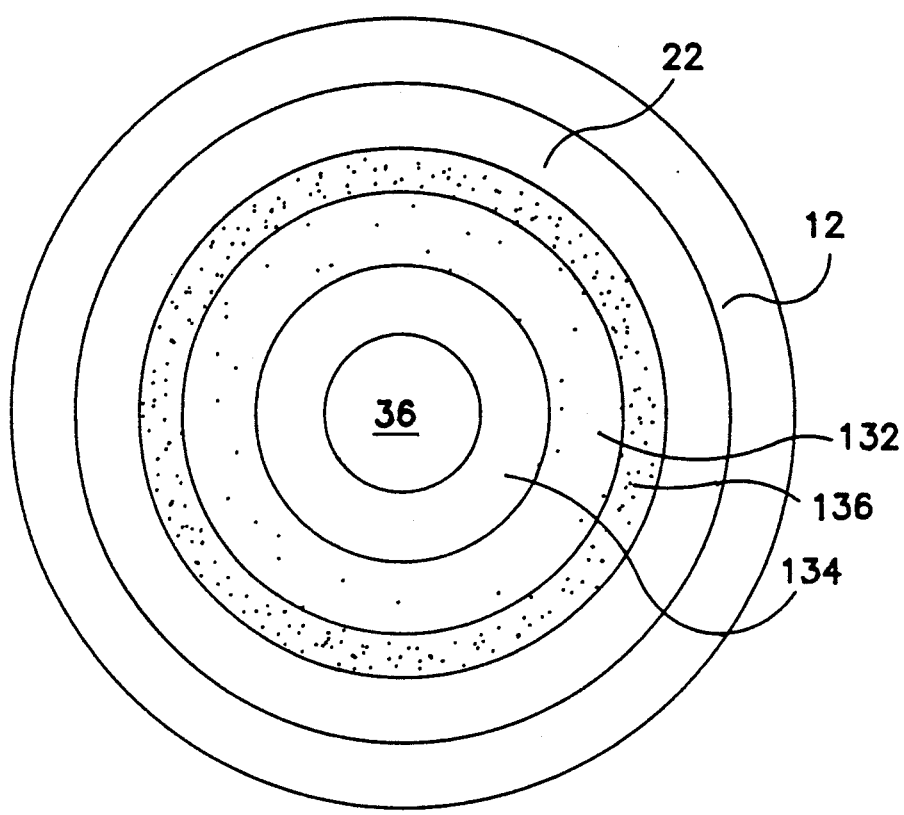
Figure 3E:
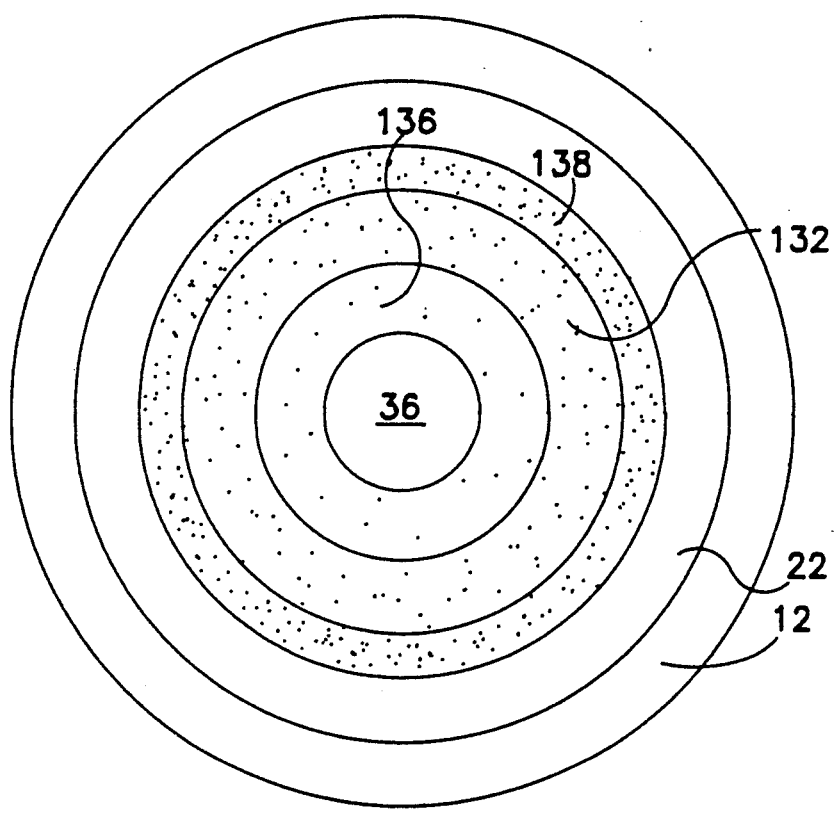

FIG. 3B is a cross-section of the rotor body taken along line 3B—3B of FIG. 3A, illustrating the suspension 130 maintained by slow rotation. In FIG. 3C, the solid phase support is shown sedimented to the inner rotor body wall to form a packed bed 132 and suspends a solution supernatant 134. In FIG. 3D, a solution 136, which is denser than the original suspension fluid, is introduced to the rotor body chamber through the lower fluid lines, displacing some of the supernatant fluid 134 out of the packed bed 132 and out of the rotor through the upper fluid line. In FIG. 3E, a still denser solution 138 is introduced to the rotor body chamber displacing all of the solution supernatant 134 and part of the intermediate density solution 136. The packed bed 132 now is partly filled with intermediate solution 136, and denser solution 138.

Figure 4:
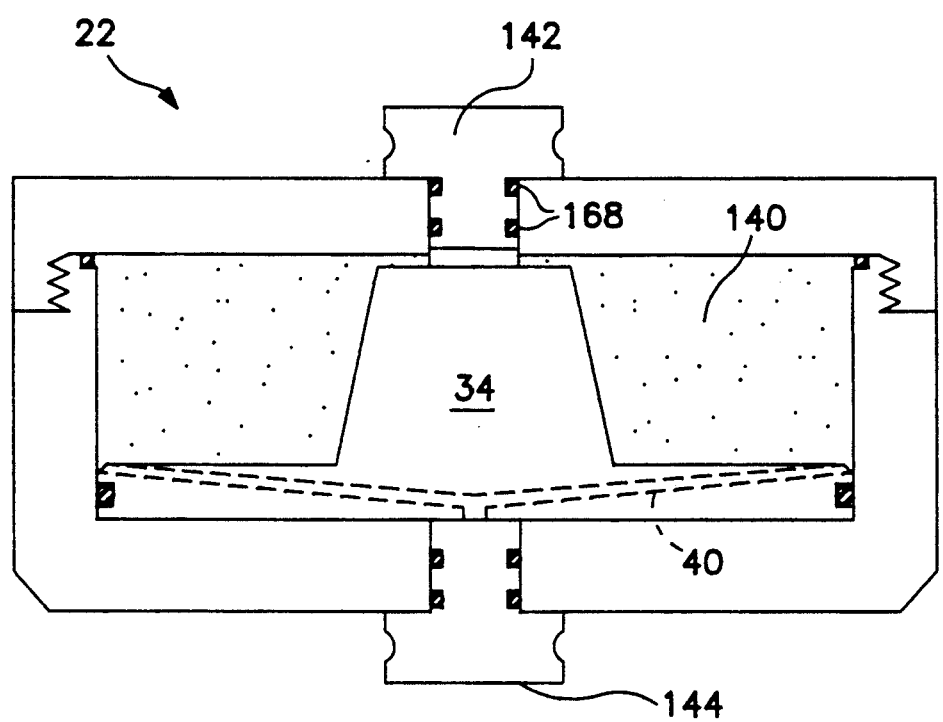
FIG. 4 illustrates a removable insert liner which is prepacked with solid phase support material.

FIG. 4 shows the chemically resistant liner 22 with the core member 34, separate from the rotor body prepacked with a solid phase support 140. Besides providing corrosion resistance for the rotor body, the liner 22 may function as an insert that can be prepacked before insertion into the rotor body. Upper and lower plugs 142 and 144 seal the contents in the liner. After use, the insert 22 can be regenerated at a separate facility.

Figure 5:
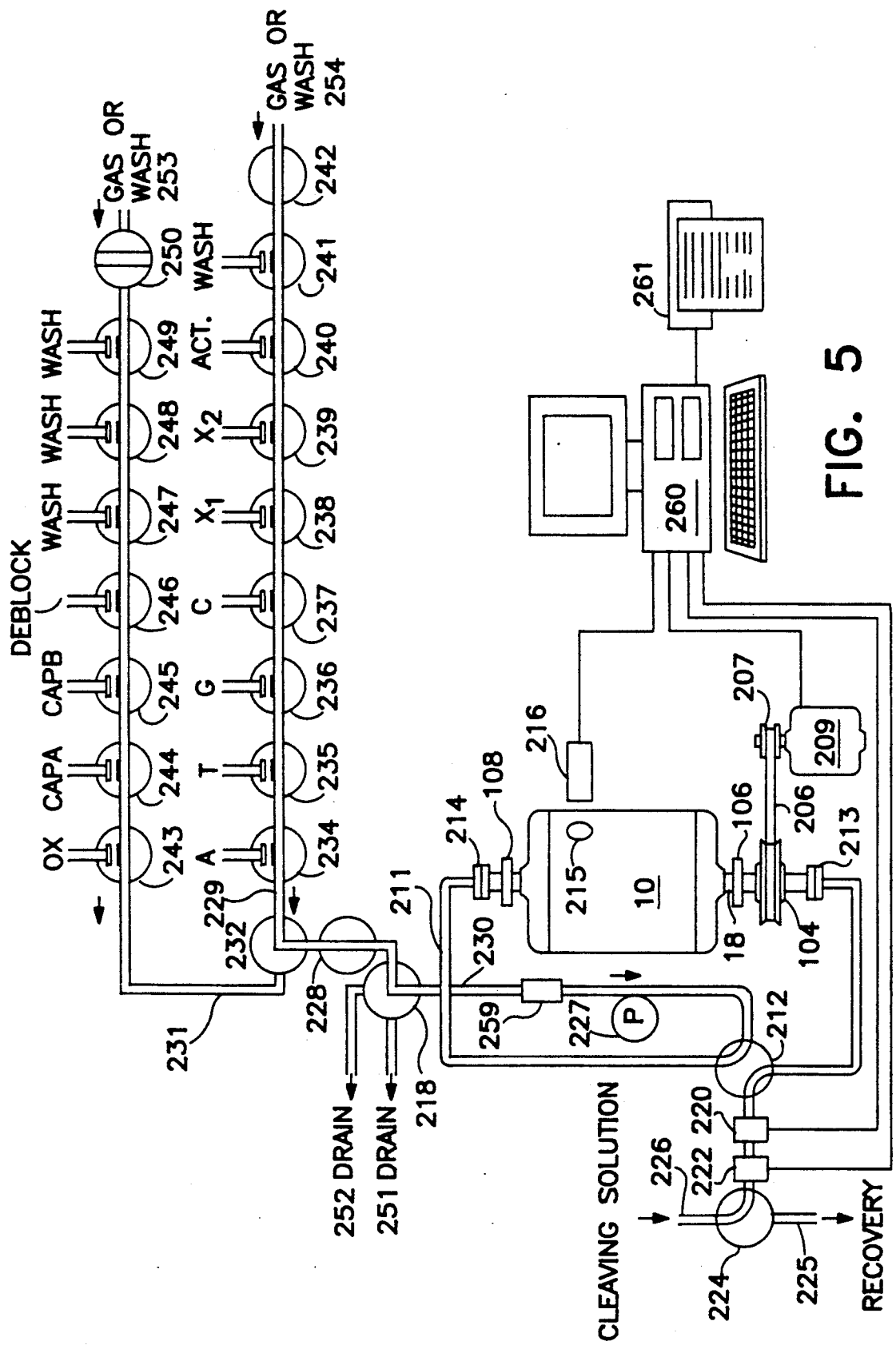
FIG. 5 illustrates a processing system that employs the centrifugal processor of FIG. 1.

FIG. 5 illustrates in schematic an example of a processing system 200 that employs the centrifugal processor 10 of FIG. 1 in order to perform a DNA or a protein synthesis. The centrifugal processor 10 is mounted in an upright position with its rotational axis aligned in the vertical. Upper and lower shaft bearings 108 and 106 couple the centrifugal processor 10 to a support (not shown). Mounted to the lower tube extension 18 of the processor 10 is the drive pulley 104 that in turn is drivingly coupled to a computer-controlled controlled drive motor 209 via a drive belt 206 and a motor drive pulley 207. A computer 260 sends command signals to the motor 209 in order to control the rotation of the centrifugal processor 10. The rotor speed may be sensed, and therefore controlled, by an optical pick-up 216 that is connected to the computer 260 and which detects a mark 215 placed on the outer surface of the centrifugal processor 10.

In operation, fluids may enter or exit the centrifugal processor 10 through an upper fluid line 211 and upper seal 214, or lower fluid line 210 and lower seal 213. Various reagents and solutions may be selectively fed to either the upper fluid line 211 or lower fluid line 210. In the embodiment shown, valves 243-250 may be electrically operated by computer 260 (through lines not shown) to deliver solutions to fluid line 231, and valves 234-242 may be operated to deliver solutions to fluid line 229. The solutions typically include washes of acetonitrile or methylene dichloride 241-242, 247-250, 253, 254, deblocking reagents 246 to remove blocking groups from a growing chain, capping reagents 244 and 245 to cap chains to which failed to add the last synthon, an oxidizing reagent 243 to oxidize phosphorus after synthon addition, synthon solutions A, T, G, and C, and modified synthons X1 and X2 through valves 234-239, and synthon activator solution added though 240. This arrangement of valves has been found convenient, and minimizes cross contamination between incompatible reagents.

Valve 232 controls the delivery of solution from fluid lines 229 and 231 to valve 228. In FIG. 5, valve 232 is shown adjusted to allow solution to flow from fluid line 229 to line 230. Valve 228 allows the reagent valve set 234-250 to be isolated from the rest of the system during the final step in the synthesis when, as explained below, the product is cleaved from the support matrix with concentrated ammonium hydroxide. Valve 218 allows solutions to be drained from the reagent valve group to waste, or allows solutions from the centrifugal processor 10 to be recovered after cleavage of the product from the support. The solution in line 230 may in turn be delivered to either the lower fluid line 210 or upper fluid line 211 by activating reversing valve 212. With valve 212 in the position shown, the solution in line 230 flows to upper fluid line 211 and into the centrifugal processor 10.

In the configuration shown, fluid exiting the centrifugal processor 10 is delivered to lower fluid line 210. This exiting fluid is directed by reversing valve 212 to a liquid density sensor 220 and optical sensor 222 for analysis before being delivered through valve 224 to a recovery vessel through line 225 or to waste. Control and flow reversal valve 212 may also be positioned so that the reagents and solutions are delivered to the lower fluid line 210 and fluids exiting the centrifugal processor through upper fluid line 211 are delivered to the recovery 225. Consequently, the system 10 can be easily adjusted so that denser fluids are directed to the lower port of centrifugal processor 10, whereas less dense inflowing fluids are directed to the upper port and to the rotor center.

A liquid density sensor 259 positioned in fluid line 230 detects the density of solutions received in fluid line 230 in order to provide feedback control so that if the density of the solution detected is not appropriate, density-adjusting solution may be pumped into line 230 and mixed in-line in order to adjust the density of the solution to the correct level. A pump 227 also coupled to line 230 controls the flow rate of reagents from the reagent valves into the rotor and provides the pressure required to operate the system.

The valves of the system 10 may be adjusted for cleaving the oligonucleotide product from the support within the centrifugal processor 10. Accordingly, valve 224 is positioned to allow a cleaving solution (usually concentrated ammonium hydroxide) 226 to be delivered to the system. Valve 212 controls whether the cleaving solution is delivered to the centrifugal processor 10 through the lower line 210 or upper line 211. If the valve 212 is positioned as shown, the cleaving solution is delivered to lower fluid line 210, and solution exiting the centrifugal processor 200 is delivered to fluid line 230 via upper fluid line 211 and valve 212. Control valve 218 is adjusted so that the cleaving solution in fluid line 230 is delivered to recovery 251. During the cleaving process, valve 228 is closed. Line 225 ordinarily leads to drain, however in some synthesis procedures (the H-phosphonate procedure for example) synthons may be recovered, repurified, and reused.

Washing solutions 253 and 254 may be run through lines 231 and 229, respectively, and with the proper adjustment of valves 232, 228, and 218, be delivered to drain 252 to remove any reagents which may be in these lines. A printer 261 is provided to provide hard copy data relative to each synthesis done. Note that valves 234 to 249 are three way valves which are always open to through passage, but with the third port normally closed and only opened to add the reagent controlled by that valve.

Figure 6:
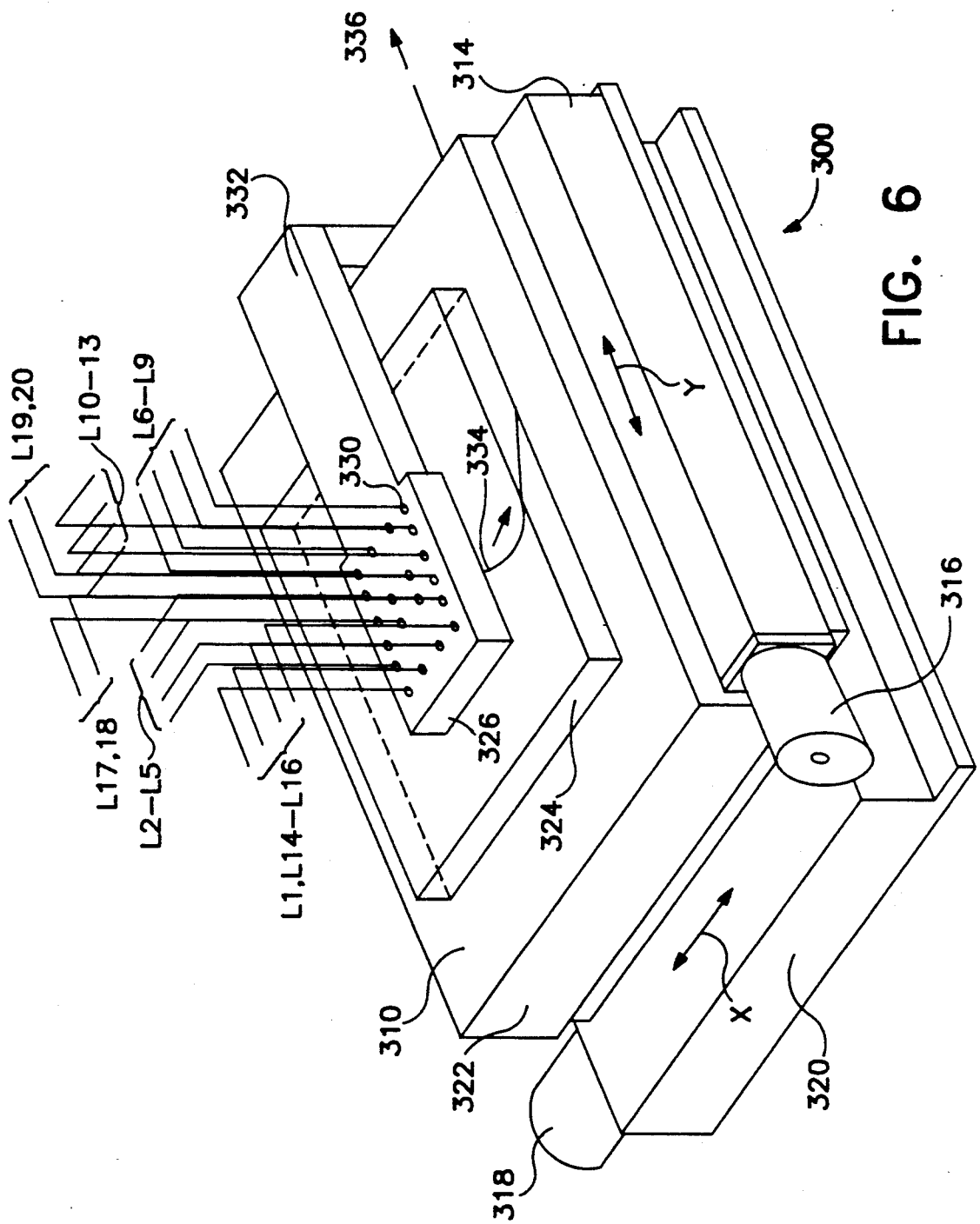
FIG. 6 is a perspective view of a flat, sliding, multi-port valve that may be used in connection with the centrifugal processor.
Figure 7:
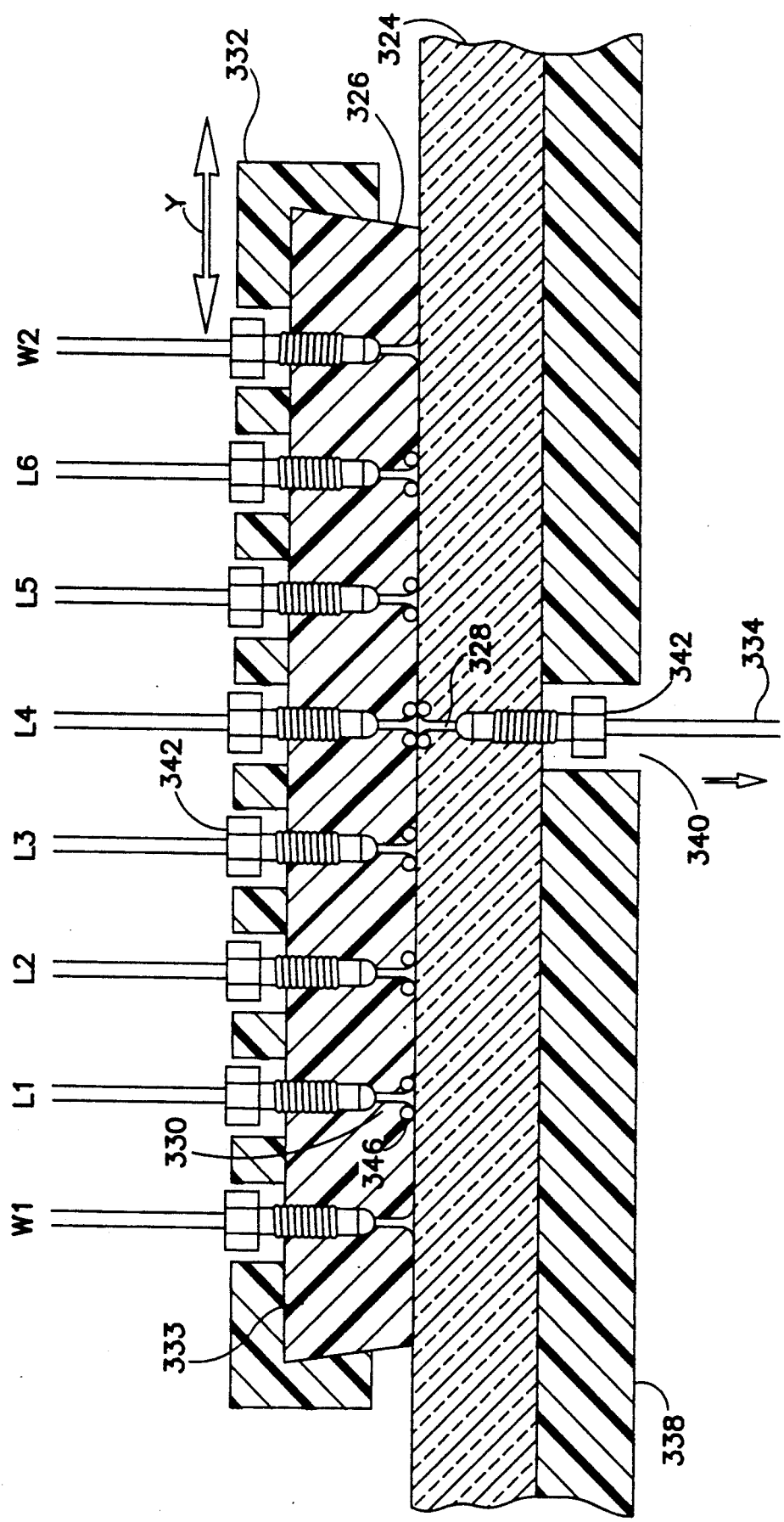
FIG. 7 is a partial cross-sectional view of the valve plate and glass plate of the valve of FIG. 6.
Figure 8:
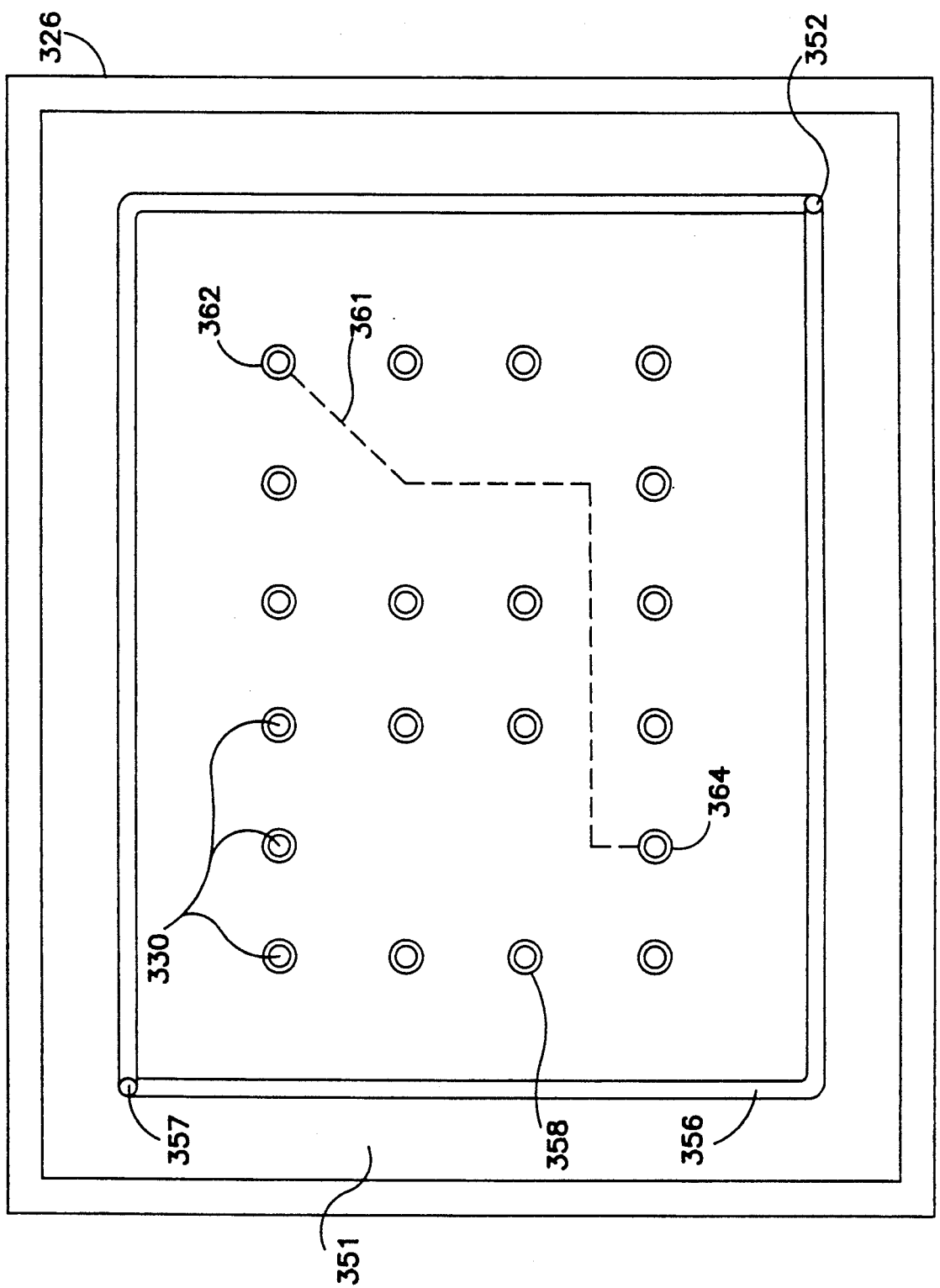
FIG. 8 is a sectional view of the valve illustrating the underside of the valve plate.

FIGS. 6-8 illustrate a flat sliding multi-port valve 300 that may be used to selectively deliver reagents and solution to a centrifugal processor such as the processor discussed above. One or more valves 300 may be used in place of the valves and fluid lines 229, 231-250 of the system 200 shown in FIG. 5. Valve 300 has zero hold-up volume, eliminates the need for running a washing solution through a system in order to prevent undesirable mixing of the agents and solutions, and is a random-access connecting system. Furthermore, one component, as explained below, is a glass plate, so consequently, the system can be arranged so that its operation can be viewed directly.

The valve 300 comprises a rectangular open frame 310 that is adapted for sliding movement in mutually perpendicular directions as represented by arrows X and Y. Coupled to one side of the open frame 310 is a linear actuator 314 that is drivingly coupled to a stepper motor 316. Activation of the stepper motor 316 causes the actuator 314 to incrementally move the frame 310 in the Y direction. Similarly, a stepper motor 318 and linear actuator 320 are coupled to side 322 of the frame 310 in order to move the frame in the X direction. As shown in FIG. 6, the Y stepper motor 316 and actuator 314 are elevated with respect to the X stepper motor 318 and actuator 320. The result is that open frame 310 can be moved under computer control to any position within its normal travel. Open-frame X-Y movements are well known in the art and are commercial products.

Mounted on top of the frame 310 is a glass or ceramic plate 324 that moves with the frame 310. Plate 324 has a single opening (the opening 328 is shown in FIG. 7) in its center which connects with a fluid line 334 that passes through the open frame 310 to external line 336. Situated above the plate 324 and in sliding relation is a fluorocarbon valve plate 326 having a plurality of through holes 330. A fixed support 332 supports the valve plate 326 in a fixed position and biases the valve plate downward into contact with the sliding plate 324. Each of the holes 330 of the plate 326 is connected to a respective fluorocarbon fluid line L1-L20.

In operation, the frame 310 and plate 324 are moved so that the single opening 328 connecting to line 334 in the center of plate 324 is aligned with one of the openings 330 in the valve plate 326 so that a selected solution may be delivered through the valve plate 326 to external line 336 from one of the reagent and wash fluid lines L1-L20. External line 336 may then be connected to a centrifugal processor (not shown).

FIG. 7 illustrates a partial cross-sectional view of the valve plate 326 and glass plate 324. As shown, the valve plate 326 includes the fluorocarbon block member 333 and the compressive support 332. Also shown is the sliding glass plate 324 with the centrally located opening 328. Beneath the glass plate 324 is a metal pressure plate 338, mounted to the frame 310 of FIG. 6, that functions as a spring to bias the plate 324 upward in opposition to the bias produced by the support 332 so that the fluorocarbon block member 333 and glass plate 324 are tightly held together. The metal pressure plate 338 has a bore 340 that is aligned with the opening 328 in the glass plate 324. Disposed within the openings 330 of the valve plate 326 and the opening 328 are fittings 342 to connect the fluorocarbon lines W1,W2, L1-L16, to the fluorocarbon block member 333, and glass plate 324 to line 334. Note that connections to the glass require either the use of machinable glass, or a threaded glass-filled fitting or other special means to achieve a leak-tight connection between the fluorocarbon tube 334 and the glass or ceramic plate.

Each outlet L1-L6 on the fluorocarbon plate 333 enlarges in the area of contact with the glass to accept a sliding O-ring 346, usually of resistant fluoroelastomer. Glass plate 324 is coated with a very thin coat of fluorocarbon polymer by pressing it against this plastic at an elevated temperature. Lines W1 and W2 are for solvent under pressure to insure that a thin fluid film exists between the plates, and to wash away any leakage should it occur. Note that for leakage to occur between reagents, the reagents must pass two O-ring seals, and pass between flat plates, one of fluorocarbon, the other fluorocarbon-coated, which are under some pressure. Unfilled fluorocarbon plastics cold flow, therefore plate 326 is advantageously fabricated from a fluorocarbon plastic filled with glass or other resistant material. If leakage presents any problem with these valves, two concentric O-rings in place of one may be placed around each reagent port.

FIG. 8 illustrates the underside of valve plate 326 as viewed from between fluorocarbon plate 326 and glass or ceramic plate 324 of FIG. 7. A total of twenty-two holes are shown, of which twenty holes 330 preferably are for reagents, and two holes 352 preferably are for wash solutions. Ports 352 are each connected to solvent lines W1 in order to keep groove 356, formed in the bottom surface of the valve plate 326, filled with solution under a slight pressure. The remaining holes 330 connect to specific reagent or solvent lines. Each reagent hole has, at the bottom surface 351 of the plate 326, a circular groove 358 to accept a small O-ring. The surface 351 is flat and has a polish obtained by pressing a fluorocarbon against polished glass, quartz, or ceramic at a temperature near its softening point.

A major purpose of this design is to allow random access to all reagent lines. By sliding the upper valve plate 326 of the sliding valve shown in FIGS. 6-8 across the lower glass plate 324 so that the opening 328 in the lower glass plate 324 traverses, for example, the path shown by the dotted line 361, sequential connections may be made between holes 362 and 364 or any other pair of reagent holes, without making passing connections with any other lines.

Figure 9A:
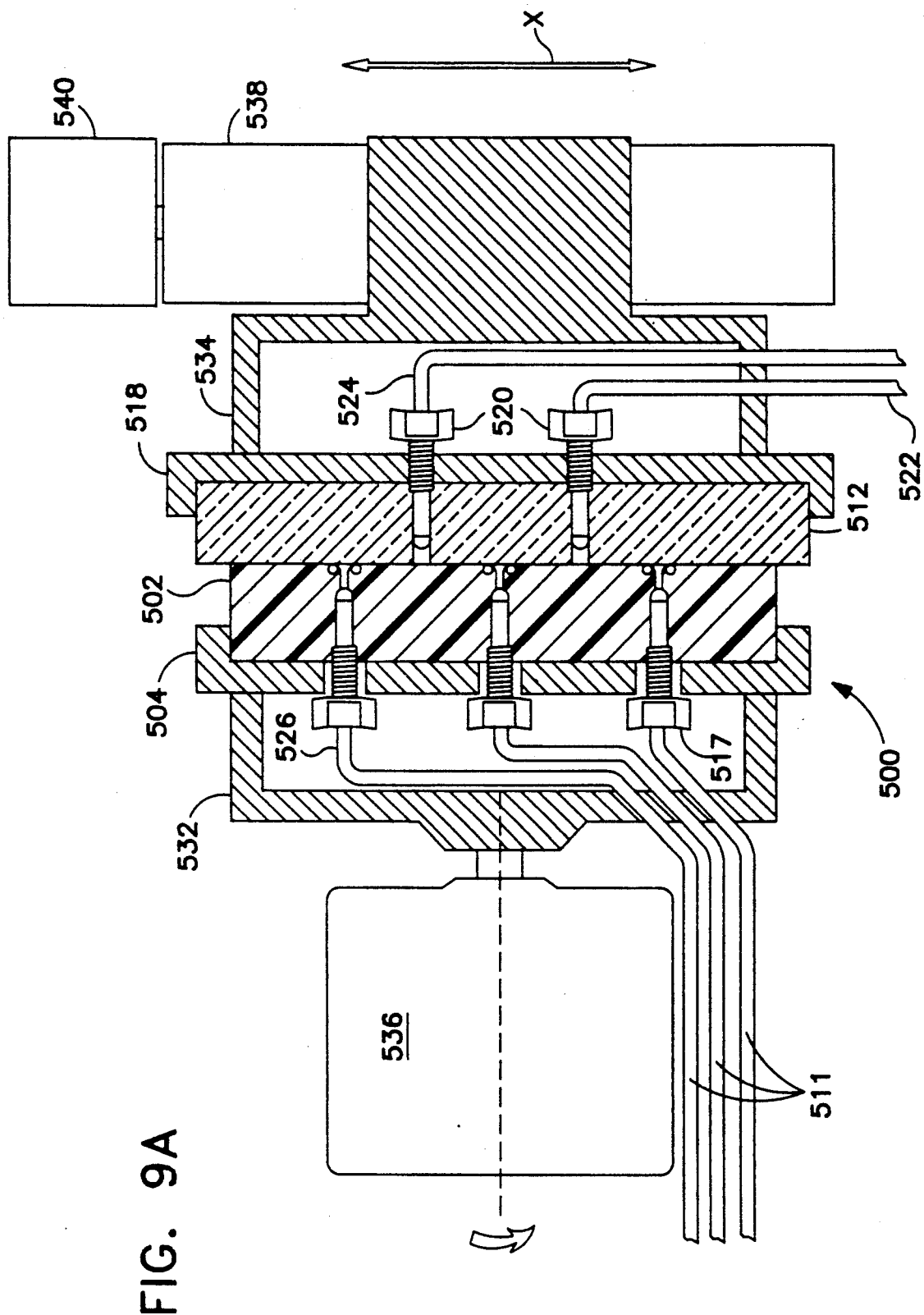
FIG. 9A is a sectional view of an alternate embodiment of a multi-port valve having one member which rotates and another member which translates in a linear direction.
Figure 9C:
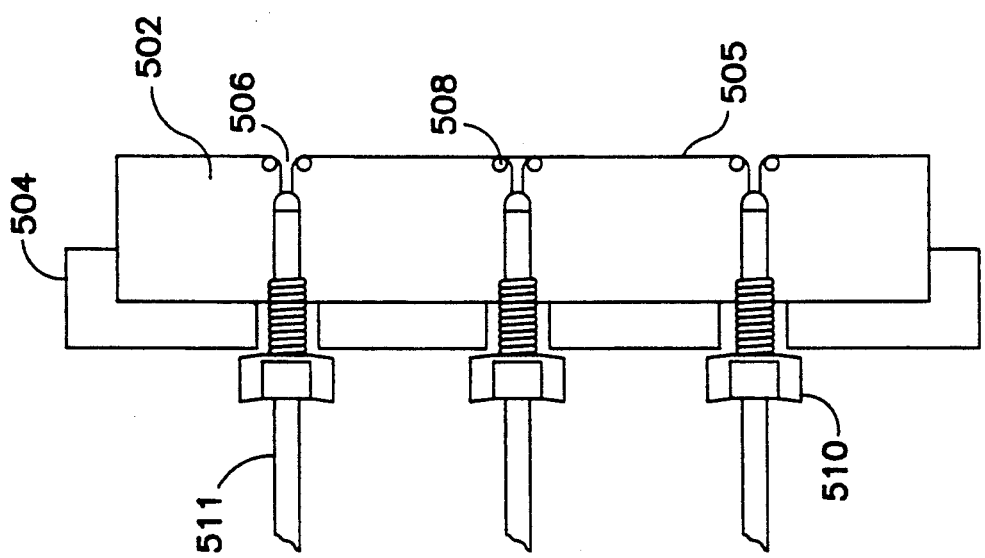
FIG. 9C is a sectional view of the rotating member, taken along line 9C—9C of FIG. 9B.
Figure 9B:
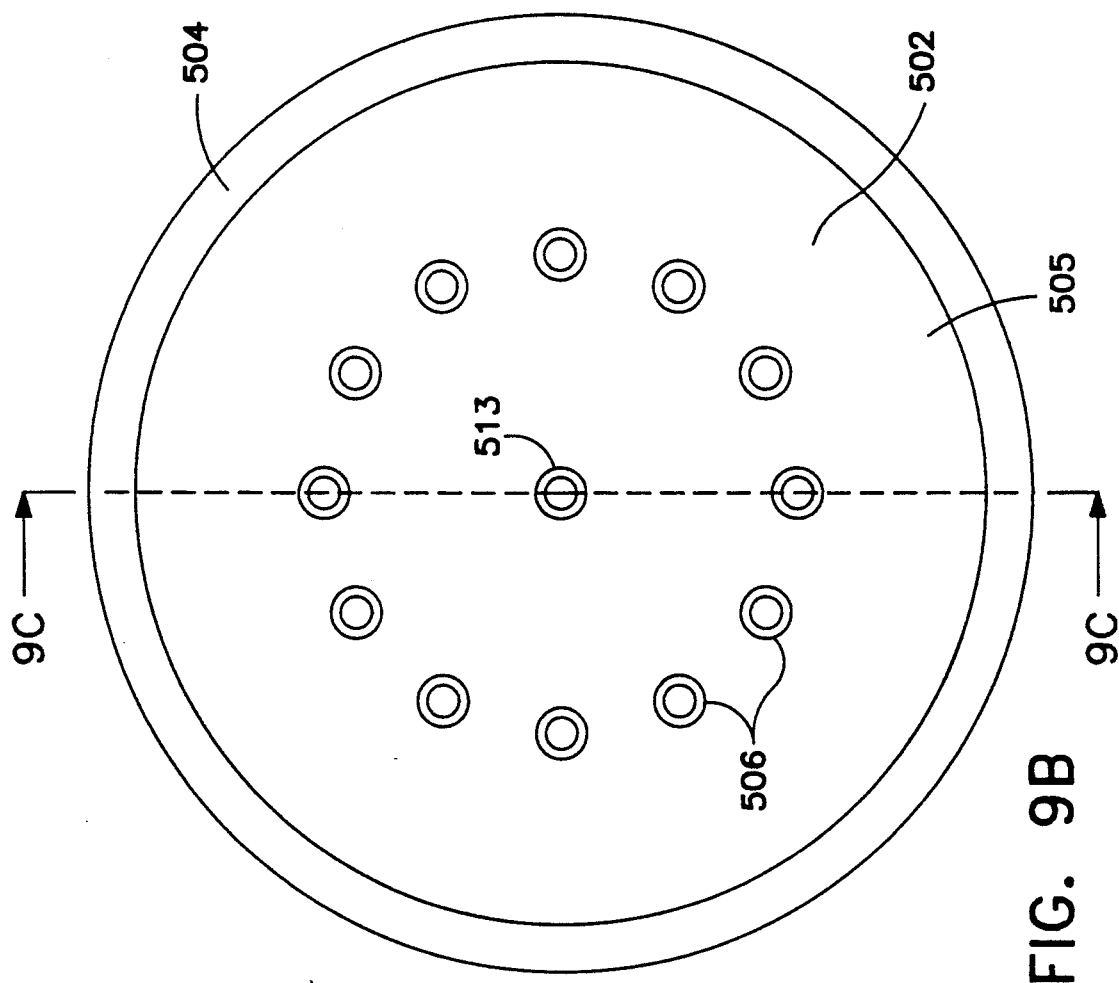
FIG. 9B is a plan view of the rotating member.

FIGS. 9A-9G illustrate an alternative design of a flat random-access multi-port valve 500. With reference to FIG. 9A, the valve 500 comprises a round, flat multi-port plate 502 made of fluorocarbon which is pressed against a round glass plate 512. The fluorocarbon plate 502 is shown in plan view in FIG. 9B and is shown in side cross-sectional view in FIG. 9C, as taken along line 9C—9C of FIG. 9B. The fluorocarbon plate 502 is supported by a perforated metal plate 504. Openings 506 in the plate 502 have O-ring recesses and O-rings 508 and connectors 510 which connect the apertures 506 to fluorocarbon tubes 511. As shown in FIG. 9B, the O-ring sealed apertures 506 are arranged to form a ring with all apertures substantially at the same radius and evenly disposed in a circle. An additional aperture is provided in the center. All of the circumferentially-arranged apertures 506 are connected to sources of reagents and solvents, with the fluid flowing thrugh the holes in the direction toward the plate surface 505.

Figure 9E:
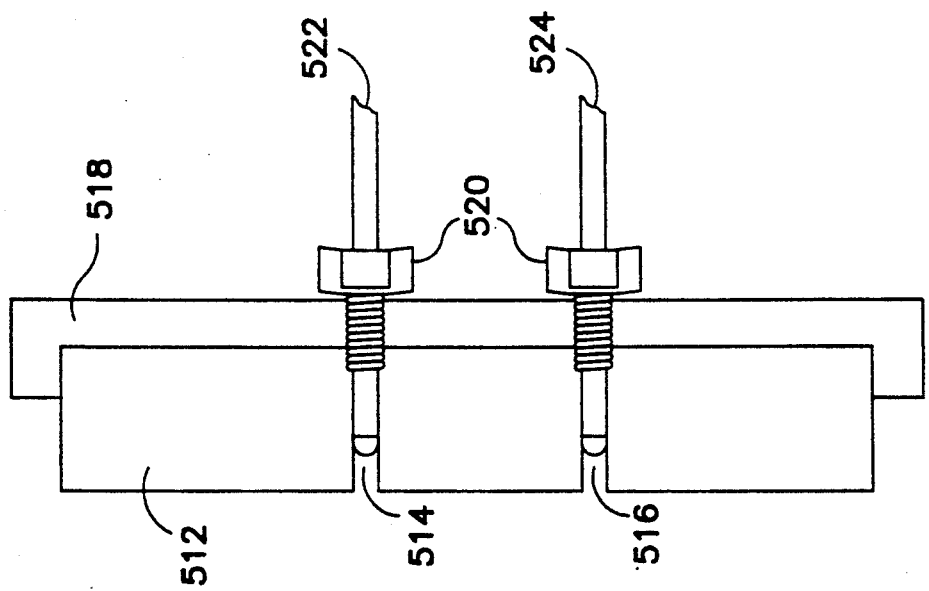
FIG. 9E is a sectional view of the translational member, taken along line 9E—9E of FIG. 9D.
Figure 9D:
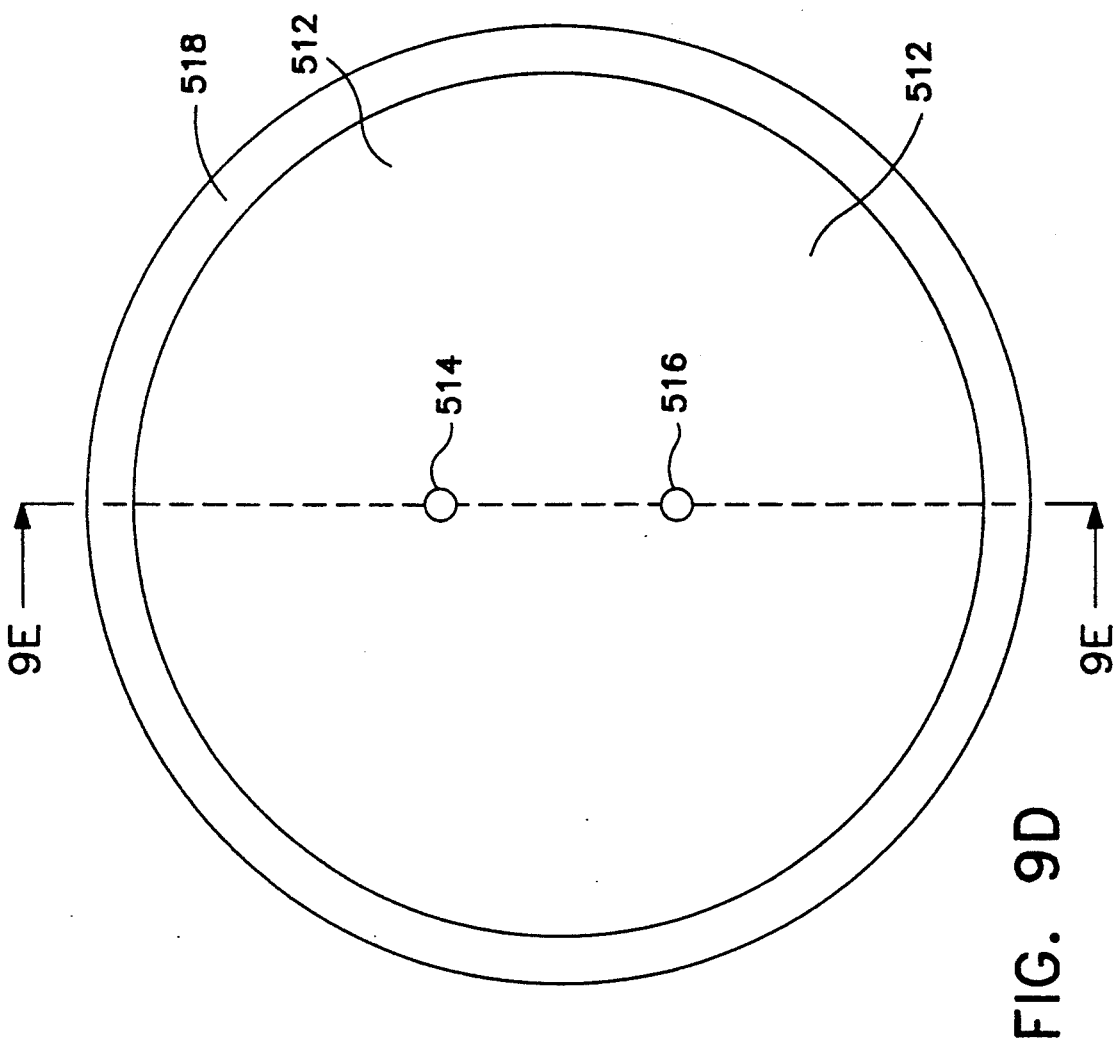
FIG. 9D is a plan view of the translational member of the valve.

The glass or ceramic plate 512 is illustrated in plan view in FIG. 9D and in cross-sectional view in FIG. 9E. The plate is supported by a metal pressure plate 518 which works in opposition to the metal plate 504 of the fluorocarbon plate 502 in order to compress the fluorocarbon and glass plates together. The glass plate 512 is provided with two openings 514 and 516. The openings are not provided with O-rings, but do have their edges polished in order to prevent damage to overlying O-rings when the glass and fluorocarbon plates are in sliding contact. The openings have connectors 520 which connect the openings 514 and 516, respectively, to fluorocarbon fluid lines 522 and 524. Line 522 may be coupled to the upper center opening of a centrifugal processor according to the present invention, whereas fluid line 524 may be connected to the lower fluid port. Connections between the glass plate 512 and fluorocarbon lines 522 and 524 may be made using threaded connections and machinable glass, with fittings under compressed force obtained by screwing adaptors 520 through the plate 512, or by drawing the fluorocarbon tubing out when softened by heat and then drawing it through the polished holes in the glass plate until the section in the plate is under strong compressive force because it has a larger diameter than the hole in plate 512.

Two movements are required to operate the valve 500. The first is rotation of the multi-port fluorocarbon plate 502 about its central axis, and the second is translation of the glass plate 512 in a radial direction with respect to the multi-port fluorocarbon plate 502. To achieve rotational movement of the fluorocarbon plate 502, the plate 502 is coupled to a stepper motor 536 through a supporting arbor 532. The plate 502 can be rotated through 360°. However, the plate should not be rotated through more than 360°, or else the fluid lines 511 might become tangled. Within the 360°, however, the fluid lines 511 can wind and unwind without kinking. The opposing glass or ceramic plate 512 and metal plate 518 are coupled to a linear actuator 538 and stepper motor 540 through arbor 534. The linear actuator and stepping motor 540 drive the plate 512 in a translational direction, as shown by arrow X in FIG. 9A.

Figure 9F:
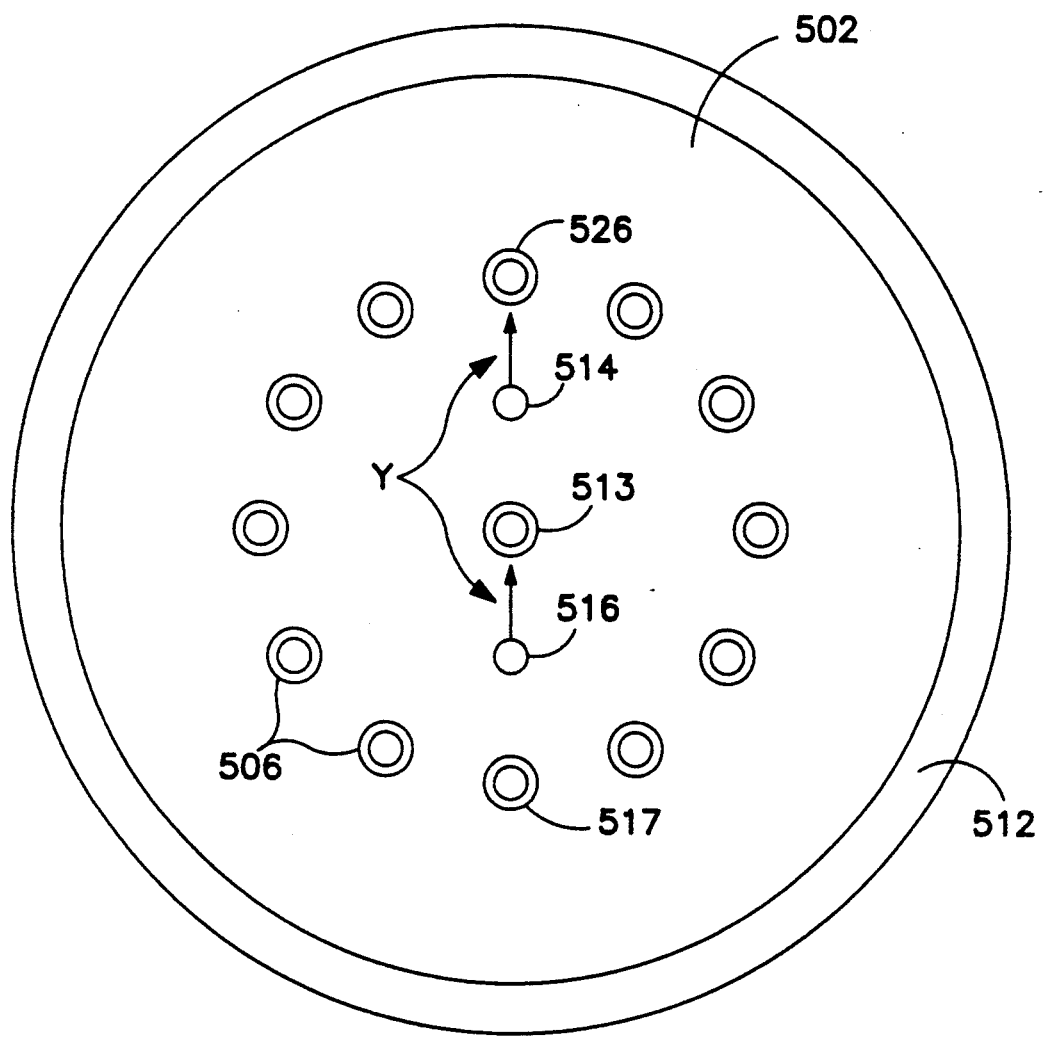
FIG. 9F is a schematic diagram of the valve in a closed position.
Figure 9G:
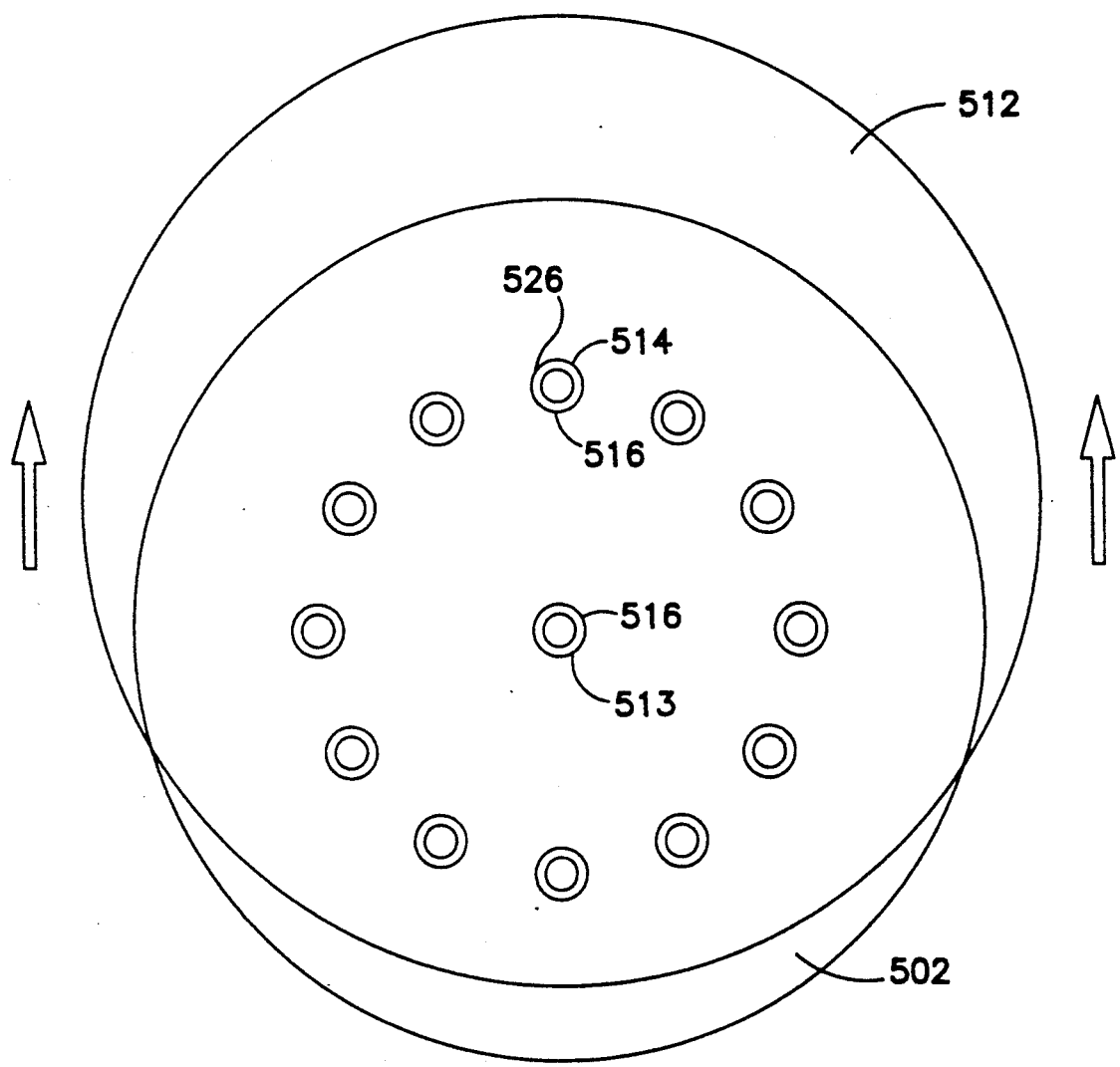
FIG. 9G is a schematic diagram illustrating the multiport valve in an open position.

FIG. 9F illustrates schematically the positions of the holes in both the fluorocarbon and glass plates 512 and 502 when the plates are centered and compressively opposed. In such a position, all of the openings of each plate are sealed closed by the surface of the opposing plate. The two openings 514 and 516 in the glass plate 512 occupy positions halfway between the center hole 513 of the fluorocarbon plate 502 and the circumferential holes 506. The two-holed glass plate 512 is larger than the fluorocarbon plate 502. If the glass plate 512 is moved in a translational direction, as indicated by the arrow Y, the glass plate hole 514 will move into alignment with the fluorocarbon plate hole 526, and likewise hole 516 will move in alignment with the center hole 513 of the fluorocarbon plate. This alignment is illustrated in FIG. 9G.

In this position, reagent flowing into opening 526 of the fluorocarbon plate 502 will flow out of the opening 514 of the glass plate, through fluid line 524 to the upper port of the centrifugal processor. Fluid flowing through line 522 through the opening 516 of the glass plate 512 flows through the center opening 513 of the fluorocarbon plate 502 and to a drain or collection line. By rotating the multi-port fluorocarbon plate 502 relative to the two-port glass plate 512, and then translating the glass plate relative to the fluorocarbon plate 502, either the upper port or lower port of the centrifugal processor can be connected to any of the circumferential reagent lines or to the center drain or collection line. Thus, the system is a random access valve, a flow reversing valve, and a zero-dead volume valve with no cross-contamination due to apertures traversing open ports. Note that between all connective steps the valve is returned to a position such as that illustrated in FIG. 9F, where no lines are connected. The number of ports shown on the fluorocarbon plate is for illustration only, and greater or lesser numbers of ports may be used. Other arrangements of holes are within the scope of the valve described.

Figure 10:
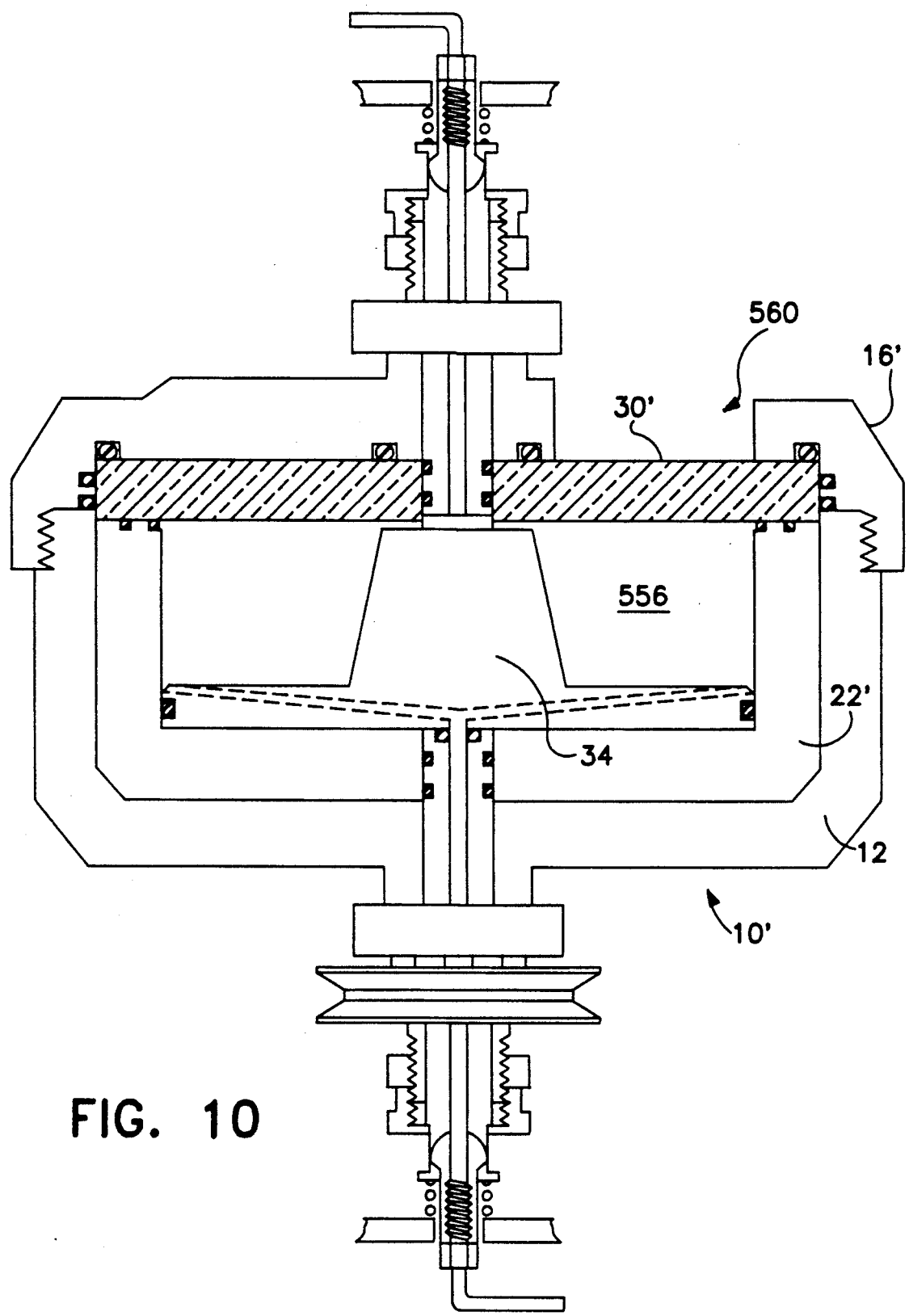
FIG. 10 illustrates an alternate embodiment of the centrifugal processor, configured so that the contents thereof may be observed and monitored.

FIG. 10 illustrates a variation of the centrifugal processor 10 of FIG. 1. The centrifugal processor 10' is similar in construction to the processor 10 of FIG. 1, with the exception that the liner 22' has a substantially flat transparent cap 30' and the end cap 16' of the rotor body has an aperture 560. Accordingly, the movement of fluid zones through the packed bed can be observed and measured during rotation of the centrifugal processor 10'.

Construction of Rotating Process Systems

For most chomatographic work, stainless steel rotor construction with filled fluorocarbon (Rulon, for example), and conventional stainless steel and plastic valves suffice. In some instances, the rotors may be fabricated from aluminum and anodized. For oligonucleotide and peptide synthesis, however, a variety of reagents are employed which have deleterious effects on most metals and plastics. The reagents used include dichloroacetic acid, trifluoroacetic acid, acetic anhydride, methylene chloride, acetonitrile, dimethylaminopyridine, tetrahydrofuran, lutidine, iodine, and 28% ammonium hydroxide. Few materials are resistant to all of these and they include glass, quartz, polypropylene (although not ideal), solid fluorocarbon polymers (Teflons), Kel F, and fluoroelastomers such as Kalrez, which is inert to all reagents employed. Polypropylene can be used for orienting studies, but it lacks the long term stability of Teflon and its derivatives. Teflon and versions of it cold flow, causing problems when they are part of a rotation system that must be sealed. However, glass-filled Teflon is available and does not cold flow.

While titanium metal is resistant to nearly all of these (the exception being chlorinated and fluorinated acids), it is difficult and expensive to machine. When the dwell time for chlorinated or fluorinated acids is limited, use of titanium rotors may prove useful. Titanium-palladium alloys are also suitable. The rotating processor according to the present invention is therefore preferably constructed with fluorocarbon interiors supported by an outer metal shell.

Methods of Use of the Rotating Processor System

The general principles involved in the synthesis of polypeptides or oligo- or polynucleotides are well known in the art. Examples of such general principles are presented in numerous patents, including U.S. Pat. Nos. 4,458,066, 4,517,338 and 4,631,211, and British Patent No. 2,194,176, all of which are incorporated by reference herein.

In very general terms, the process of synthesizing polypeptides or oligo- or polynucleotides is based on the fact that such compounds comprise chains of particular subunits. Polypeptides comprise chains of amino acid subunits and oligo- and polynucleotides comprise chains of nucleotide subunits. Thus, the general concept involved in the synthesis of these chain compounds is the sequential addition of the desired subunits until the desired chain is complete.

In solid phase synthesis, a series of reagents flow sequentially past a solid phase support. Part of this series is repetitive, consisting of addition of the next nucleotide, washing, capping of failure sequences, washing, oxidation of trivalent phosphorous to pentavalent phosphorous, washing, and then repetition of the series. Separate and unique steps initiate and terminate the series. These are initial activation of the support, and cleavage of the synthesized oligonucleotide from the support. For many purposes, the product must be further purified.

While the composition of the reagents may be changed as the process is improved and refined, certain requirements remain fixed. These include the requirement for a non-leaking support, for effective washing between steps, for the absence of moisture or oxygen from the system at certain steps, for introduction of reagent volumes within certain specified volume ranges (precise quantitative pipetting is not necessary), and for very pure reagents to minimize side reactions. The latter requirement greatly increases cost. Since trace contaminants cause side reactions, not only is high purity required, but methods for increasing washing efficiency, and for quantitatively replacing one reagent by the next are also required.

1. Oligonucleotide Synthesis

Three general methods have been employed for the solid phase synthesis of DNA. These include the triester method of Gait and Itakura (*Nucl.Acids Res.* 8:1081 (1980); *Science* 198:1056 (1977)), the methyl phosphoramidite system of Carruthers (*Tetrahed. Letts.* 22:1859 (1989)), and more recently, the cyanoethyl phosphoramidite method (Newton, R., *ABL*, pp 41–45, May 1989)). In all of these methods, it is essential to exclude water during the coupling step. The use of the present system is described employing the cyanoethyl phosphoramidite method, although the present system can be used for any of the other methods as well. The series of reactions to be performed are:

1. Activation and attachment of the first nucleotide (controlled-pore glass (CPG) is commercially available with the first nucleotide already attached, making this step unnecessary in practice.)
2. De-tritylation of the 5' end of the support-bound nucleotide.
3. Acetonitrile wash.
4. Addition of the next nucleotide for coupling in the presence of an activator.
5. Acetonitrile wash.
6. Capping of failure sequences.
7. Acetonitrile wash.
8. Oxidation of the trivalent phosphorous link to a pentavalent phosphorous.
9. Acetonitrile wash.
10. Repeat steps 2–9 to attain required chain length.
11. Cleavage of the chain from the support with 38% ammonia.
12. Removal of protective groups.
13. Purification by chromatography or electrophoresis.
14. Concentration of the oligonucleotide and reduction to dryness.

The support is usually controlled-pore glass, and the cleaved chains are usually left overnight in ammonia at 55°–60° C. to remove the cyanoethyl group as well as protective groups present in the original phosphoramidites. If purification is required, the product is adsorbed on a small reverse phase column, the failure sequences eluted, after which the dimethoxytrityl (DMT) group, by which the product is adsorbed to the column, is removed from the support-bound oligonucleotides. Alternative methods of purification include gel electrophoresis, chromatography, and hybridization to oligonucleotides attached to solid supports followed by elution at a higher temperature. The completely deprotected and recovered product is eluted and lyophilized. The approach is outlined in Table I.

TABLE I

Chemical Steps for one Synthesis Cycle

| Step | Reagent or Solvent | Purpose | Time (min) | Density g/ml |
|---|---|---|---|---|
| i (a) | Dichloroacetic acid in $CH_2Cl_2$ (2:100, v/v) | Detrityl-ation | 3 | |
| (b) | $CH_2Cl_2$ | Wash | 0.5 | 1.325 |
| (c) | Acetonitrile | Wash | 1.5 | 0.714 |
| (d) | Dry acetonitrile | Wash | 1.5 | 0.714 |
| ii (a) | Tetrazole activated nucleotide in acetonitrile | Add nucleo-tide | 5 | |
| (b) | Acetonitrile | Wash | 0.5 | 0.714 |
| iii (a) | DMAP:THF:lutidine (6:90:10, v/v/v) in acetic anhydride | Capping of failure sequences | 2 | |
| (b) | THF:lutidine:$H_2O$ (2:2:1, v/v/v) | Wash | 1 | |
| iv (a) | THF:lutidine:$H_2O$ (2:2:1, v/v/v) containing 0.2 M iodine | Oxidation | 1 | |
| (b) | Acetonitrile | Wash | 0.5 | 0.714 |
| (c) | $CH_2Cl_2$ | Wash | 0.5 | 1.325 |

DMAP = dimethylaminopyridine
THF = tetrahydrofuran

Note that there are multiple washes with the same solvent between wash steps. Different synthesizer manufacturers use slight modifications of the above procedure, which can be adapted to the present invention.

Density modifications are required for using a rotating processor (centrifugal synthesizer), according to the present invention, so that solutions may be introduced during rotation either to the rotor center or to the rotor edge. When a series of solutions of decreasing density are being used they are introduced through the center (upper) seal and line, while solutions of increasing density are introduced through the lower seal which leads to rotor edge line. In either series a point is reached where the flow must be reversed so that one may go down in density during flow through the center line, and back up in density during flow to the edge. The procedures of Table I are modified to give the densities required for zonal stability, and as necessary in the entire series to make the flow reversals.

Note that the deprotection (detritylation) step is done using dichloroacetic acid (density 1.563 g/ml) in $CH_2Cl_2$ (1.325 g/ml), making the deprotection solutio physically the most dense. The subsequent washes are first in $CH_2Cl_2$, and then acetonitrile which has a density of 0.714 g/mL at room temperature. By adding a small amount of $CH_2Cl_2$ to the acetonitrile washes i(c) and i(e), they may be made denser than the subsequent synthon solution ii(a). The synthon solution may actually be denser than the subsequent acetonitrile solution, hence an acetonitrile wash ii(b) may also be included in the descending density series and be the last solution in it. Hence, the solutions in i(a) to ii(a) may be arranged to have sequentially decreasing densities, and would be introduced through the rotor center. It has been found that $CH_2Cl_2$ can be substituted for acetonitrile in the process. This fact suggests that adjustment of density by adding $CH_2Cl_2$ to acetonitrile will have negligible effect on the synthetic yield. The series from ii(b) to iv(a) appear, on first inspection, to be a series of increasing density with the exception of acetonitrile in iv(b) which can be mixed with some methylene dichloride to give an intermediate density. The position of iii(a) in this series remains to be worked out and may be the first in the increasing density series. With the modifications introduced, flow would be through the center line from i(a) to ii(b), and through the edge line from iii(a) through to repeat i(a).

The reason for attempting to minimize flow reversals is to minimize the total volume of reagents consumed since the last reagent before flow reversal must completely fill the rotor, with some excess flow. Waste reagent disposal is expensive, and is one of the problems to be solved in scale up. Decreasing the total volume of reagent used helps solve this environmental problem.

Similarly, the phosphite triester method can be adapted for the synthesis of oligonucleotides which have phosphorous, sugar, and base modifications (as are required for the synthesis of antisense compounds) in the rotating processor described above.

Therefore, solutions are moved through the rotor in zones which have volumes which may be very much smaller that the rotor volume. A zone of oxidizing solution may require more than one minute to traverse the rotor volume, but if the zone is sufficiently thin, any one CPG particle may be arranged to be exposed to it for only one minute. Sectorial dilution must be compensated for, and flow rates may have to be carefully controlled and monitored during passage of key solutions through the rotor.

In small-scale systems, some of the steps are as short as 30 seconds. A large reaction bed cannot be filled and emptied in that time period. However narrow reagent zones, which would diminish the reagent exposure time of any given particle to such a short interval can be arranged, and are generally followed by extended washes. Flow reversals should occur either after introduction of reagents which can be present for an appreciable period of time, or after washes where a few extra minutes are of no consequence. If flow reversal after i(a) in the above example is a problem, highly chlorinated or fluorinated non-ionic organics are available to add to i(b) to make it the most dense solution, thus controlling the exposure time to i(a).

Suitable solid phase support matrix materials have been extensively described in the art, such as U.S. Pat. No. 4,631,211 (incorporated herein by reference) which describes polymerized resins in the form of porous beads. A variety of such supports have been described, and will continue to be described. These have been largely superceded by controlled-pore glass, the preferred material for oligonucleotide synthesis.

The extent of the reaction taking place in the bioprocessor may be monitored by sensors at the entry to the processor and at the exit from the processor. These sensors may monitor the solutions entering and exiting the processor based on well-known physical and/or chemical characteristics of the solutions. Examples of such physical and/or chemical characteristics which may be monitored include density, light absorption, and pH. The monitoring of the entry and exit of various solutions from the bioprocessor may be coordinated and adjusted through the use of a microprocessor. By monitoring the optical absorbance of the effluent during and after coupling for trityl groups, the efficiency of coupling can be determined.

2. Peptide Synthesis

A variety of supports have been described for peptide synthesis which include the original polystrene resins of Merrifield (available from Sigma Chemical), controlled-pore glass (available from CPG Inc), a synthetic porous material called Polyhype (Bachem), a support based on acrylamide gel attached to kieselguhr (Applied Biosystems and Millipore), and numerous others. For the present purposes the only requirement is that flow through them can be controlled in a centrifugal field, and the excessive clogging of frits does not occur.

A series of modified reagents which have been used for the centrifugal synthesis of peptides is shown in Table II, together with the function of each and their liquid densities. The repetitive cycle is from steps 3 to 9. This reagent set was constructed for use with the proprietary resin Polyhype which floats in solutions having densities above 1.17 g/mL. Therefore the initial step 1 has the highest density, and would be introduced from the rotor edge. The remaininq solutions through 7 are of decreasing density and would be introduced through the rotor center. Flow is reversed before solution 8 is introduced (inflow is through the edge line), and again after step 9 (inflow from the center), and the sequence is then continued cycling through steps 3 to 9.

When synthesis is complete, steps 10 to 16 are completed, and the product is recovered in trifluoracetic acid. Subsequent purification may also be done using rotating processors for desalting, chromatographic purification, ending in a large rotary evaporator.

TABLE II

Sequence of Solutions Used for Initial Synthesis, and their Densities

| Solution Number or Step | Function | Solution Composition (W/W) | Density g/ml, 24° C. |
|---|---|---|---|
| 1. | Initial wash | 70% DCM + 30% DMF | 1.168 |
| 2. | Initial Deprotection | 60% DCM + 20% DMF + 20% piperidine | 1.143 |
| 3. | Wash | 50% DCM + 50% DMF | 1.095 |
| 4. | Wash | 30% DCM + 70% DMF | 1.030 |
| 5. | Coupling | 0.3 mM Fmoc amino acid 0.3 mM TBTU 0.6 mM DIPEA 0.3 mM Hobt in 6 ml of 20% DCM + 80% DMF (for 0.1 mM solid support) | 1.000 |

TABLE II-continued
Sequence of Solutions Used for Initial Synthesis, and their Densities

| Solution Number or Step | Function | Solution Composition (W/W) | Density g/ml, 24° C. |
|---|---|---|---|
| 6. | Wash | 10% DCM + 90% DMF | 0.973 |
| (6A* | Capping | Acetic Anhydride and Pyridine Centrifugal drainage at this step if capping is done. | 0.960) |
| 7. | Wash | 100% DMF followed by centrifugal drainage cycles 2X | 0.946 |
| 8. | Deprotection and Density Increase | 60% DCM + 20% piperidine + 20% DMF. This is introduced twice with centrifugal drainage between. | 1.143 |
| 9 | Wash | 70% DCM + 30% DMF | 1.168 |
| 10. | Wash | 60% DCM + 40% DMF | 1.130 |
| 11. | Wash | 30% DCM + 70% DMF | 1.030 |
| 12. | Wash | Methanol | 0.791 |
| 13. | Wash | 2-Propanol | 0.785 |
| 14. | Wash | Ethyl ether | 0.714 |
| 15. | Drying | Flush with Argon or $N_2$ | — |
| 16. | Cleavage | 95% Trifluoroacetic acid (TFA) | 1.50 |

*Optional
DCM = Dichloromethane
DMF = Dimethylformamide
HBOT = hydroxybenzotriazole
TBTU = 2-(H-benzotriazol-1-yl)-1,1,3,3—tetramethyluronium tetrafluoroborate
DIPEA = N,N-Diisopropylethylamine
TFA = trifluoroacetic acid.

These reagents have been found to be useful in the successful centrifugal synthesis of peptides related to sequences found in HIV.

Density adjustments may also be made using the very dense reagent hexafluoro-2-propanol (d=1.596 g/ml) which has been described as a solvent for peptide synthesis (*Int. J. Peptide Prot. Res.* 36:193 (1990)).

3. Chromatographic Separations

The number of different chromatographic separations which are known in the art, and which can be adapted to the rotating processor of the present invention is very large. These fall, for the purposes of the present discussion, into two groups which are those using isocratic elution (i.e., conditions do not change during elution), and those which use step or continuous gradients, or a combination of them. Truely isocratic elution is not adaptable to a rotating processor because the solutes eluted alter the density of the solutions used, and lead to zone instability and loss of resolution. Isocratic conditions can be reproduced however, if a density gradient is superimposed which does not alter the elution parameter, as then a sucrose gradient is superimposed on a solution of constant salt composition. For gradient elution under conditions where the gradient increases in density, edge to center flow is used for elution, and a gradient of a non-interactive material may be superimposed to increase zone capacity in the gradient. In numerous types of elution, especially in protein purification, salt gradients are used which produce increasing density. Other elution conditions involve a decrease in density, as for example, when a water-acetonitrile gradient is used for the separation of proteins such as wheat gliadins. Acetonitrile has a density of 0.714 g/ml at 20° C., hence, water to acetonitrile gradients are stable in a rotating process or when introduced through the center line in a rotor previously filled with water or with a dilute aqueous salt solution.

4. Synthesis and Separation

Rotary processors can also be used to sequentially synthesize a ligand which remains immobilized in the processor and is then used to purify a solute passed through the rotor. For example, olignucleotides can be synthesized as described above, using attachments to the solid phase support which are not broken during deprotection. The deprotected and immobilized oligos can then be used to selectively hybridize with DNA or RNA in solution, and to remove from the stream only those which match. By changing solvent conditions and/or temperature, the contaminants can be first eluted, followed by the selected product. With long oligonucleotides, for example 20 mers, this process may not be sufficiently selective. Hence, shorter oligonucleotides nucleotides can be synthesized, for example 8 mers, and used to isolate matching sequences. By using three or more overlapping short sequences, each of which are selective in sequence, highly purified sequence-specific oligonucleotides can be obtained.

An additional example is the use of peptides which have been synthesized in the processor and which remain immobilized in the solid phase matrix, to isolate by reverse affinity chromatography monospecific antibodies against the synthesized peptide. Thus, proteins, including antibodies, enzymes, hormones, receptors, and all other types of proteins, nucleic acids, and a variety of intermediate and low molecular weight compounds may be separated and purified in rotating processors. In addition, nucleic acids and oligonucleotides may be purified by selective hybridization and elution.

As previously described, two or more rotary processors can be utilized in series. Thus, for example, one rotary processor can be utilized to synthesize an oligonucleotide and one or more rotary procesors can be used to purify the oligonucleotide as previously described.

While the invention has been disclosed in this patent application by reference to the details of preferred embodiments of the invention, it is to be understood that this disclosure is intended in an illustrative rather than limiting sense, as it is contemplated that modifications will readily occur to those skilled in the art, within the spirit of the invention and the scope of the appended claims.

What is claimed is:

1. A system for solid phase reactions comprising:
   rotor means for performing a solid phase reaction in the presence of a solid support matrix, said rotor means comprising a rotor body capable of rotating about a rotational axis and defining an inner chamber, said rotor body having a first central, axial fluid passage connecting the inner chamber to the outside of said rotor body and a second fluid passage opposite said first passage and having an opening to said inner chamber adjacent a radially-outward, inner wall surface of the rotor body;
   a solid support matrix;
   means for retaining said matrix in said rotor means;
   means coupled to said rotor means for introducing selected fluids of sequentially differing densities to one of either said first or second passage and removing fluid from the other of said first or second passage; and means for ordering said fluids of sequentially differing densities to allow for either introduction of fluid gradually or stepwise increasing density into said rotor body through said second passage such that fluid phases of different density are formed in said chamber and move toward said rotational axis, forcing less dense fluid out said first passage or introduction of fluid of gradually or stepwise decreasing density into said rotor through said first passage such that fluid phases of different density are formed in said chamber and move radially outward, forcing denser fluid out said second passage.

2. The system of claim 1, wherein the rotor body is operated with the axis horizontal, and the rotor body is rotated slowly or oscillated to suspend and agitate the particulate material while the rotor body is filled with a fluid causing one step in a synthetic reaction.

3. The system of claim 1, wherein the rotor comprises an outer housing and an inner sealed liner constructed of chemically inert material.

4. The system of claim 3, wherein the inner chamber is removable, and is prepacked with a solid support matrix.

5. The system of claim 1, wherein the solid support matrix, fluids, fluid introduction and removal means, and composition of the rotor.

6. The system of claim 1, wherein said means for introducing selected fluids comprises a flat multi-port valve having a plurality of openings connected to reagent lines on a flat face of a first plate thereof, and a single opening connected to the rotor body on a flat face of a second plate thereof, wherein one face comprises an inert plastic and the other face is made of glass, quartz, sapphire, or ceramic material, said valve having motor means for programmed X-Y motion of one face relative to the other, such that the single opening may be aligned with any opposing one of said ports in any order without cross contamination.

7. The system of claim 6, wherein both plates have more than one opening.

8. The system of claim 7, wherein one of the plates is rotated to bring the openings into alignment, and the other plate is translated radially, relative to the first, to produce alignment to give a valve which is both random-access and flow reversing.

9. The system of claim 6, wherein two flat multi-port valves are coupled to the rotor means, one immediately above the rotor means and the other immediately below the rotor means, so that when liquids of decreasing density are introduced through the upper valve, or of increasing density through the lower valve, no density inversions occur in the lines.

10. The system of claim 6, wherein the position of the valve openings are readily visible to the operator through the plate which is transparent.

11. The system of claim 1, wherein one end of the rotor is transparent.

12. The system of claim 1, wherein the axis of rotation may be changed either during rotation or at rest.

13. The system of claim 1, wherein the rotor core has radially arranged vanes which are perpendicular to the axis of rotation.

14. The system of claim 1, further comprising a microprocessor to control rotor body speed and entry of the fluids into the rotor body.

* * * * *